(12) United States Patent
Bosua et al.

(10) Patent No.: US 12,059,239 B2
(45) Date of Patent: Aug. 13, 2024

(54) ELECTROMAGNETIC SHIELDING IN NON-INVASIVE ANALYTE SENSORS

(71) Applicant: Know Labs, Inc., Seattle, WA (US)

(72) Inventors: Phillip Bosua, Seattle, WA (US); Steven Kent, Seattle, WA (US)

(73) Assignee: Know Labs, Inc., Seattle, WA (US)

( * ) Notice: Subject to any disclaimer, the term of this patent is extended or adjusted under 35 U.S.C. 154(b) by 0 days.

(21) Appl. No.: 18/160,235

(22) Filed: Jan. 26, 2023

(65) Prior Publication Data

US 2023/0172476 A1 Jun. 8, 2023

Related U.S. Application Data

(63) Continuation of application No. 17/889,102, filed on Aug. 16, 2022, and a continuation of application No. 17/123,992, filed on Dec. 16, 2020, now Pat. No. 11,903,689, said application No. 17/889,102 is a continuation of application No. 16/741,428, filed on
(Continued)

(51) Int. Cl.
| | |
|---|---|
| *A61B 5/0507* | (2021.01) |
| *A61B 5/00* | (2006.01) |
| *A61B 5/145* | (2006.01) |
| *A61B 5/1455* | (2006.01) |
| *H05K 9/00* | (2006.01) |
| *A61B 5/107* | (2006.01) |

(52) U.S. Cl.
CPC .......... *A61B 5/0507* (2013.01); *A61B 5/0075* (2013.01); *A61B 5/14532* (2013.01); *A61B 5/14552* (2013.01); *A61B 5/1071* (2013.01); *A61B 5/14546* (2013.01); *A61B 5/681* (2013.01); *A61B 5/6831* (2013.01); *H05K 9/0081* (2013.01)

(58) Field of Classification Search
CPC . A61B 5/0507; A61B 5/0075; A61B 5/14532; A61B 5/14552; A61B 5/1071; A61B 5/14546; A61B 5/681; A61B 5/6831; A61B 2562/182; H05K 9/0081; H05K 9/0024; H01L 23/60; H01Q 1/526
See application file for complete search history.

(56) References Cited

U.S. PATENT DOCUMENTS

| | | |
|---|---|---|
| 5,188,108 A | 2/1993 | Secker |
| 7,295,827 B2 | 11/2007 | Liu et al. |

(Continued)

FOREIGN PATENT DOCUMENTS

| | | |
|---|---|---|
| EP | 2457507 | 5/2012 |
| EP | 3146898 B1 | 11/2018 |

(Continued)

OTHER PUBLICATIONS

International Search Report and Written Opinion for PCT/US2019/031176, mailed Aug. 23, 2019, 9 pages.
(Continued)

*Primary Examiner* — Yi-Shan Yang
*Assistant Examiner* — Kyle W. Kretzer
(74) *Attorney, Agent, or Firm* — Merchant & Gould P.C.

(57) ABSTRACT

A non-invasive analyte sensor that includes at least one electromagnetic shield at least partially electromagnetically isolates an electrical component of the non-invasive analyte sensor from radio frequency interference and/or microwave frequency interference.

22 Claims, 13 Drawing Sheets

Related U.S. Application Data

Jan. 13, 2020, now abandoned, which is a continuation of application No. 16/405,749, filed on May 7, 2019, now Pat. No. 10,548,503.

(60) Provisional application No. 62/951,816, filed on Dec. 20, 2019, provisional application No. 62/668,567, filed on May 8, 2018.

(56) References Cited

U.S. PATENT DOCUMENTS

| | | |
|---|---|---|
| 8,223,021 B2 | 7/2012 | Goodnow et al. |
| 9,198,607 B2 | 12/2015 | Fischer |
| 9,864,024 B2 | 1/2018 | Vester |
| 10,149,629 B2 | 12/2018 | Szczepaniak et al. |
| 10,478,101 B1 | 11/2019 | Cespedes et al. |
| 10,548,503 B2 | 2/2020 | Bosua |
| 10,617,296 B2 | 4/2020 | Sloan et al. |
| 10,856,766 B2 | 12/2020 | Leabman |
| 10,912,500 B2 | 2/2021 | Poeze et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,223,383 B2 | 1/2022 | Bosua |
| 11,234,618 B1 | 2/2022 | Bosua et al. |
| 11,234,619 B2 | 2/2022 | Bosua |
| 11,244,753 B2 | 2/2022 | Haggerty et al. |
| 11,284,819 B1 | 3/2022 | Bosua et al. |
| 11,284,820 B1 | 3/2022 | Bosua et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,091 B2 | 7/2022 | Bosua |
| 11,389,093 B2 | 7/2022 | Triman et al. |
| 11,426,104 B2 | 8/2022 | Schurman et al. |
| 11,529,077 B1 | 12/2022 | Bosua |
| 11,802,843 B1 | 10/2023 | Bosua |
| 2003/0036713 A1 | 2/2003 | Bouton et al. |
| 2004/0065158 A1 | 4/2004 | Schrepfer et al. |
| 2004/0074681 A1 | 4/2004 | Ono et al. |
| 2004/0127777 A1 | 7/2004 | Ruchti et al. |
| 2004/0133086 A1 | 7/2004 | Ciurczak et al. |
| 2004/0235534 A1 | 11/2004 | Kim et al. |
| 2009/0112101 A1 | 4/2009 | Furness, III et al. |
| 2009/0275814 A1 | 11/2009 | Watanabe et al. |
| 2010/0041969 A1 | 2/2010 | Beise |
| 2011/0028814 A1 | 2/2011 | Petersen et al. |
| 2012/0053445 A1* | 3/2012 | Turnquist ............... A61B 50/00 600/407 |
| 2013/0272339 A1 | 10/2013 | Tofighi |
| 2014/0213870 A1 | 7/2014 | Hsu et al. |
| 2014/0307392 A1* | 10/2014 | Kurz .................... H05K 9/0081 361/720 |
| 2016/0051171 A1 | 2/2016 | Pikov et al. |
| 2016/0228010 A1 | 8/2016 | Kim et al. |
| 2016/0361002 A1 | 12/2016 | Palikaras et al. |
| 2017/0095667 A1 | 4/2017 | Yakovlev et al. |
| 2017/0164878 A1 | 6/2017 | Connor |
| 2017/0181658 A1 | 6/2017 | Dettmann et al. |
| 2018/0028824 A1* | 2/2018 | Pivonka ............. A61N 1/37229 |
| 2019/0008422 A1* | 1/2019 | Leath ................ A61B 5/14552 |
| 2019/0046038 A1* | 2/2019 | Weinstein ........... A61B 5/0024 |
| 2019/0053741 A1 | 2/2019 | Chaudhry |
| 2019/0104939 A1 | 4/2019 | Costantine et al. |
| 2019/0216393 A1* | 7/2019 | Baheti .................... H01L 23/66 |
| 2019/0269853 A1 | 9/2019 | Doyle et al. |
| 2019/0298208 A1 | 10/2019 | Weinstein et al. |
| 2019/0353752 A1 | 11/2019 | Lin et al. |
| 2019/0357800 A1 | 11/2019 | Bosua |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2021/0186357 A1 | 6/2021 | Bosua et al. |
| 2021/0259571 A1 | 8/2021 | Bosua |
| 2022/0015695 A1 | 1/2022 | Margarito et al. |
| 2022/0031254 A1 | 2/2022 | Al-Ali et al. |
| 2022/0071527 A1 | 3/2022 | Bosua |
| 2022/0074870 A1 | 3/2022 | Bosua |
| 2022/0077918 A1 | 3/2022 | Bosua et al. |
| 2022/0151553 A1 | 5/2022 | Bosua |
| 2022/0192494 A1 | 6/2022 | Leabman |
| 2022/0192531 A1 | 6/2022 | Leabman |
| 2022/0248984 A1 | 8/2022 | Poeze et al. |
| 2022/0346661 A1 | 11/2022 | Bosua |
| 2024/0008772 A1 | 1/2024 | Bosua |
| 2024/0011923 A1 | 1/2024 | Bosua |
| 2024/0016405 A1 | 1/2024 | Bosua |
| 2024/0074681 A1 | 3/2024 | Bosua |
| 2024/0144715 A1 | 5/2024 | Bosua et al. |

FOREIGN PATENT DOCUMENTS

| | | |
|---|---|---|
| EP | 3981329 A1 | 4/2022 |
| JP | 2012125382 | 7/2012 |
| KR | 1020160081740 | 7/2016 |
| WO | 2006138662 | 12/2006 |
| WO | 2017163245 | 9/2017 |
| WO | 2019071138 | 4/2019 |
| WO | 2019198567 | 10/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |

OTHER PUBLICATIONS

Qiang et al., "Quantitative detection of glucose level based on radiofrequency patch biosensor combined with volme-fixed structures," Biosensors and Bioelectronics 98:357-363, 2017.

Hanna, J. et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/

(56) References Cited

OTHER PUBLICATIONS history/20191118/pdf/03_quantum-op.pdf (14 pages including English translation).
Shaker, G. et al., "Non-Invasive Monitoring of Glucose Level Changes Utilizing a mm-Wave Radar System," IJMHCI, vol. 10, Issue 3 (2018): pp. 10-29 (Year: 2018).
Lien, J. et al., "Soli: Ubiquitous Gesture Sensing with Millimeter Wave Radar," ACM Trans. Graph., vol. 35, No. 4, Article 142, 19 pages (Jul. 2016) (Year: 2016).
Extended European Search Report issued for European Patent Application No. 19800864.1, dated Dec. 3, 2021, 8 pages.
International Search Report and Written Opinion issued for International Patent Application No. PCT/IB2020/062222, Date of mailing: Mar. 25, 2021, 7 pages.

\* cited by examiner

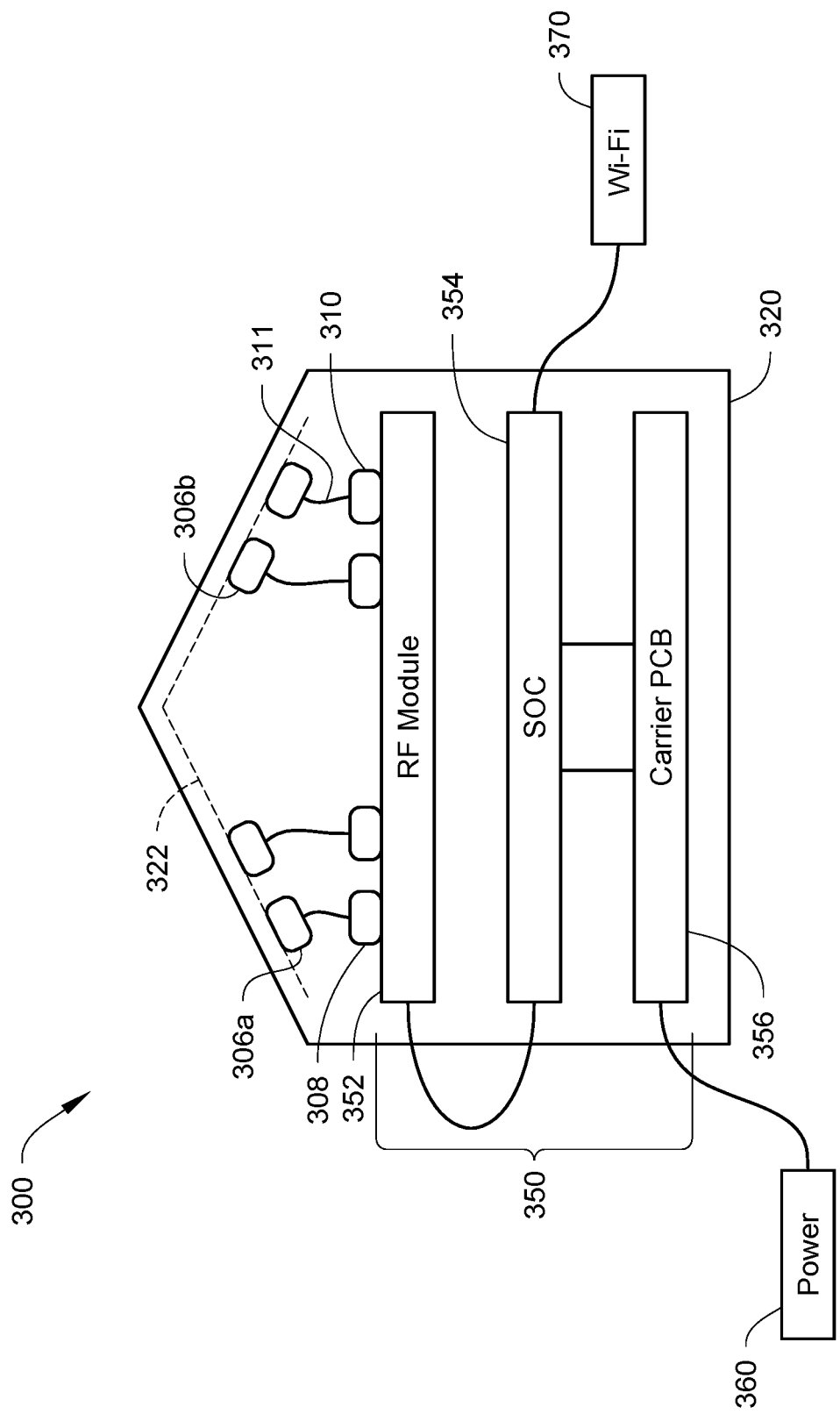

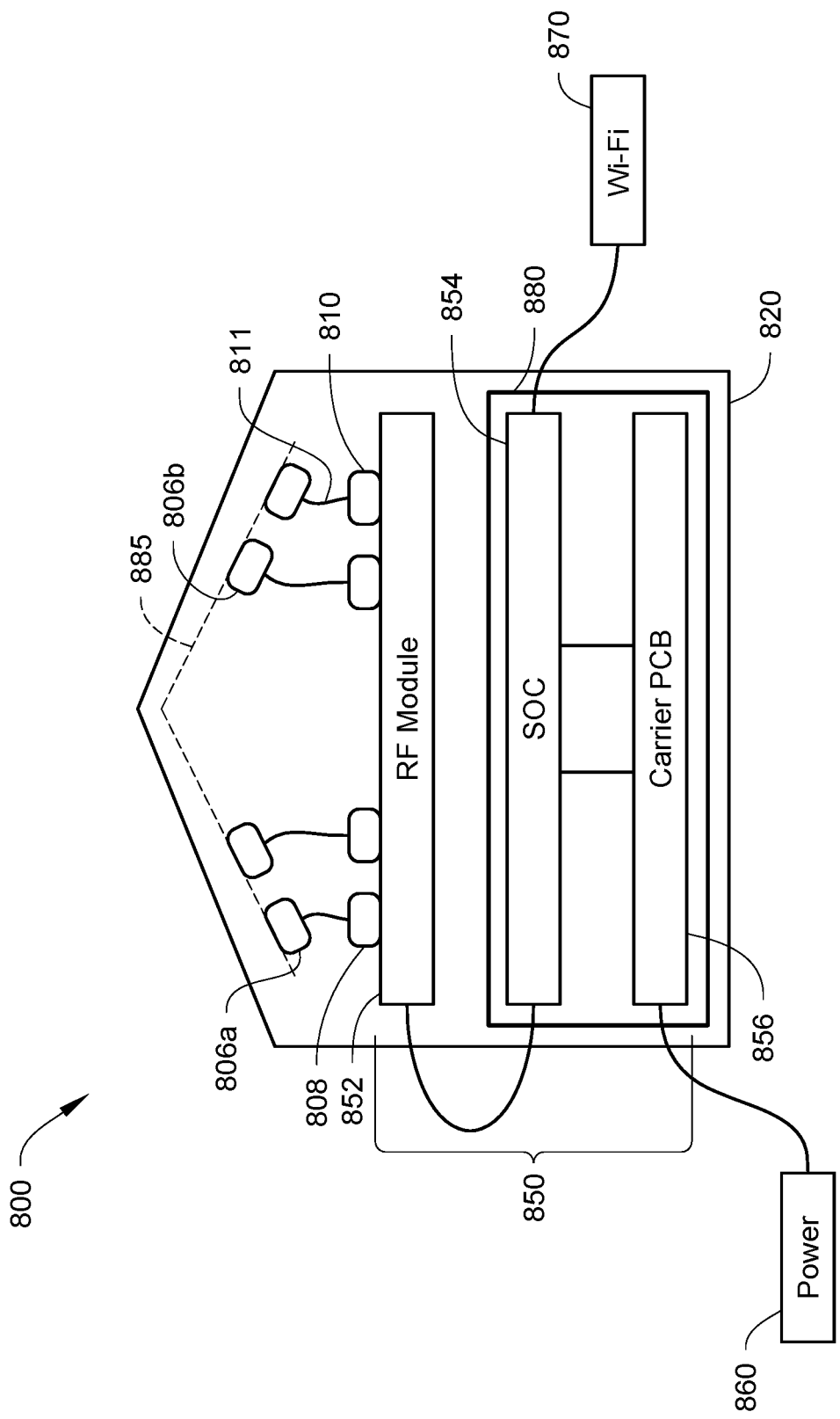

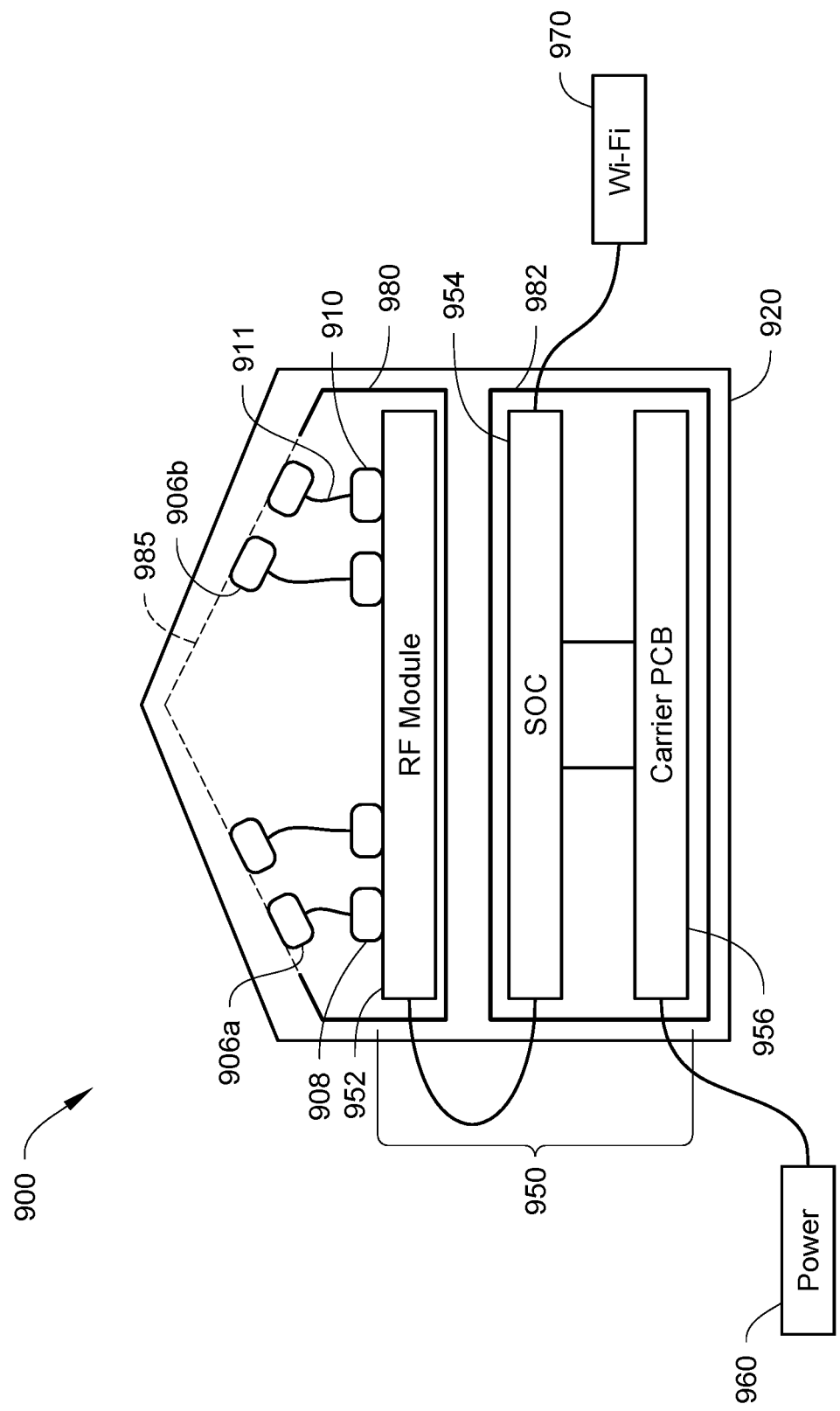

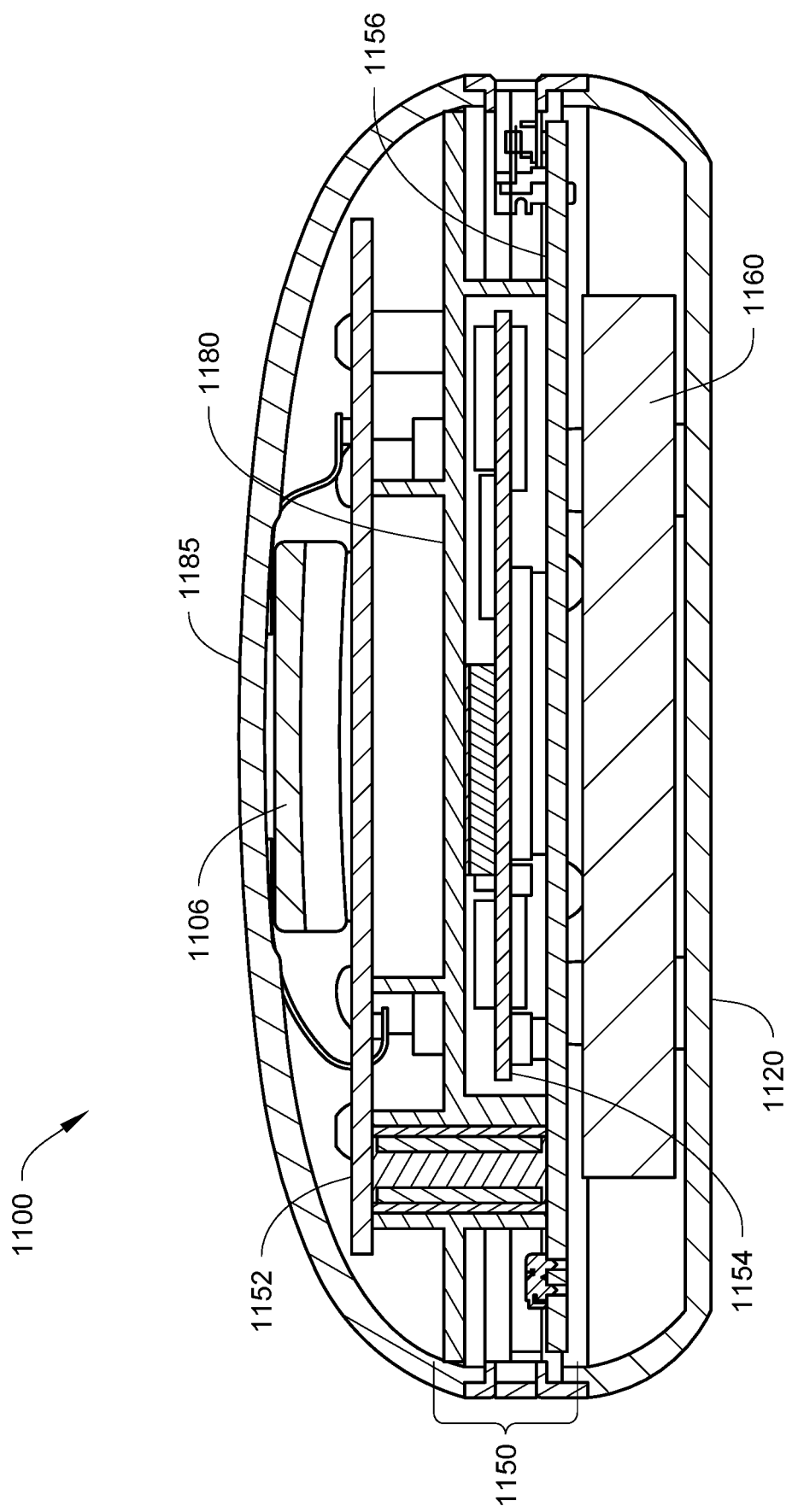

ELECTROMAGNETIC SHIELDING IN NON-INVASIVE ANALYTE SENSORS

CROSS-REFERENCE

This application is a continuation-in-part application of U.S. application Ser. No. 17/889,102, filed Aug. 16, 2022, which is a continuation application of U.S. application Ser. No. 16/741,428, filed Jan. 13, 2020, which is a continuation application of U.S. application Ser. No. 16/405,749, filed May 7, 2019 and granted as U.S. Pat. No. 10,548,503, which claims the benefit of provisional application U.S. App. 62/668,567, filed May 8, 2018, and a continuation-in-part application of U.S. application Ser. No. 17/123,992, filed Dec. 16, 2020, which claims the benefit of provisional application U.S. App. 62/951,816, filed Dec. 20, 2019, all of which are incorporated by reference in their entirety.

FIELD

This disclosure relates generally to apparatus, systems and methods of detecting an analyte via spectroscopic techniques using an analyte sensor that includes a detector array (also referred to as an antenna array), and more particularly, the detector array operating in the radio or microwave frequency range of the electromagnetic spectrum, and electromagnetically shielding the analyte sensor.

BACKGROUND

There is interest in being able to detect and/or measure an analyte within a target. One example is measuring glucose in biological material. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological material. However, many of the non-invasive methods generally suffer from: lack of specificity to the analyte of interest, such as glucose; interference from temperature fluctuations; interference from skin compounds (i.e. sweat) and pigments, e.g., melanin, haemoglobin, carotenoids, etc.; complexity of placement, i.e. the sensing device resides on multiple locations on the patient's body; and are intrusive, for example use of a blood pressure cuff. Additionally, many of these techniques are performed only on demand, for instance at a yearly physical examination or when presenting at an emergency room or urgent care facility.

SUMMARY

This disclosure relates generally to apparatus, systems and methods of detecting an analyte via spectroscopic techniques using non-optical frequencies such as in the radio or microwave frequency range of the electromagnetic spectrum. A non-invasive analyte sensor system described herein includes a detector array having a plurality of detector elements (also referred to as antenna elements or antennas) at least one of which can transmit an electromagnetic signal in the radio or microwave frequency range and at least one of which can receive an electromagnetic signal in the radio or microwave frequency range resulting from transmission of the electromagnetic signal. In the non-invasive analyte sensor described herein, at least one electromagnetic force (EMF) shield, also referred to as an electromagnetic shield, is provided on a component of the non-invasive analyst sensor to reduce and/or electromagnetically isolate a component of the analyte sensor from radio frequency interference and/or microwave frequency interference.

In one embodiment described herein, a non-invasive analyte sensor system can include a first antenna that is positioned and arranged to transmit a radio frequency transmit signal or a microwave frequency transmit signal into a target containing at least one analyte, and a second antenna that is positioned and arranged to detect a radio frequency response resulting from transmission of the radio frequency transmit signal or the microwave frequency transmit signal by the first antenna into the target containing the at least one analyte. A transmit circuit is electrically connectable to the first antenna, where the transmit circuit is configured to generate the radio frequency transmit signal or the microwave frequency transmit signal to be transmitted by the first antenna. In addition, a receive circuit is electrically connectable to the second antenna, where the receive circuit is configured to receive the radio frequency response or the microwave frequency response detected by the second antenna. At least one electromagnetic shield that at least partially electromagnetically isolates at least one electrical component of the non-invasive analyte sensor system from radio frequency interference and/or microwave frequency interference.

In an embodiment, the at least one electromagnetic shield at least partially electromagnetically isolates the first antenna, the second antenna, the transmit circuit, and the receive circuit.

In another embodiment, the non-invasive analyte sensor system further includes a system on module configured to integrate the non-invasive analyte sensor system in a single module, a printed circuit board, and a power source.

In an embodiment, the at least one electromagnetic shield at least partially electromagnetically isolates the first antenna, the second antenna, the transmit circuit, the receive circuit, the system on module, and the printed circuit board.

In an embodiment, the at least one electromagnetic shield at least partially electromagnetically isolates the transmit circuit, the receive circuit, the system on module, and the printed circuit board.

In an embodiment, the at least one electromagnetic shield at least partially electromagnetically isolates the system on module and the printed circuit board.

In an embodiment, the at least one electromagnetic shield at least partially electromagnetically isolates the first antenna, the second antenna, the transmit circuit, and the receive circuit, and at least a second electromagnetic shield at least partially electromagnetically isolates the system on module and the printed circuit board.

In an embodiment, the at least one analyte includes glucose, blood ketones, carbon dioxide, melatonin, acetaminophen, oxygen, alcohol, calcium, vitamin C, hydration, white blood cells, luteinizing hormone, or prostaglandins such as PGF2α and PGE2, hormones such as estrogen, progesterone, and/or follicle stimulating hormone (FSH).

In another embodiment described herein, a non-invasive analyte sensor system can include an antenna array having at least four antennas each of which is configured to emit and receive radio frequency electromagnetic waves or microwave frequency electromagnetic waves. A transmit circuit is selectively electrically connectable to any one or more of the at least four antennas, where the transmit circuit is configured to generate at least one transmit signal in a radio frequency range of the electromagnetic spectrum or a magnetic frequency range of the electromagnetic spectrum to be transmitted into the target by the one or more of the at least four antennas the transmit circuit is electrically connected to. A receive circuit is selectively electrically connectable to any one or more of the at least four antennas, where the receive circuit is configured to receive a response detected by the one or more of the at least four antennas the receive circuit is electrically connected to resulting from transmission of the at least one transmit signal into the target containing the at least one analyte of interest. In addition, electrical conductors electrically connect the transmit circuit and the receive circuit with the at least four antennas, and at least one electromagnetic shield at least partially electromagnetically isolates at least one electrical component of the non-invasive analyte sensor system from radio frequency interference and/or microwave frequency interference.

DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 3 is a schematic depiction of a non-invasive analyte sensor system with an analyte sensor relative to a target according to yet another embodiment.

FIG. 8 is a schematic depiction of a non-invasive analyte sensor system with an electromagnetic shield according to yet another embodiment.

FIG. 9 is a schematic depiction of a non-invasive analyte sensor system with an electromagnetic shield according to another embodiment.

FIG. 11 is an illustration of a non-invasive analyte sensor system with an electromagnetic shield according to another embodiment.

Like reference numbers represent like parts throughout.

DETAILED DESCRIPTION

Figure 1:
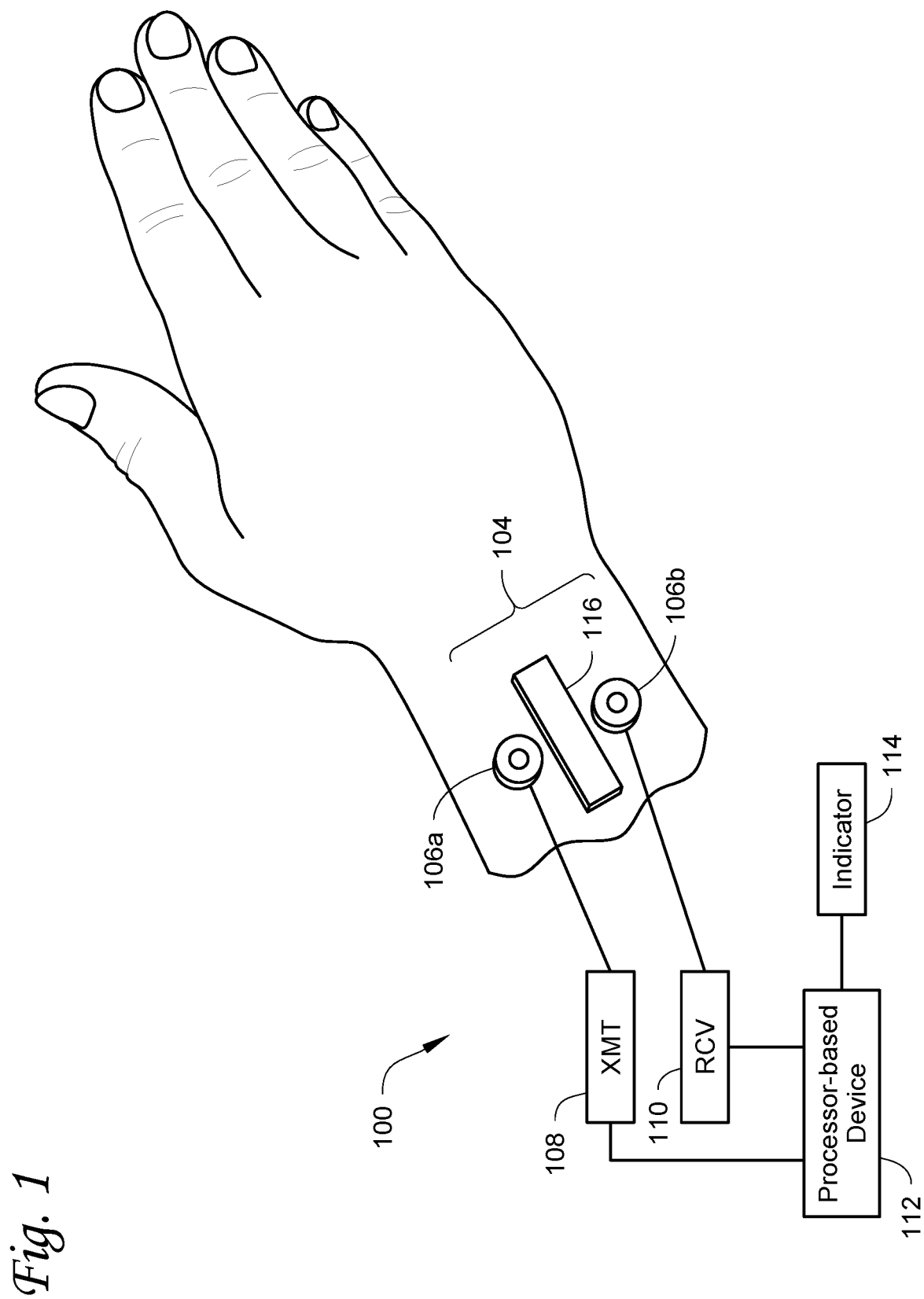
FIG. 1 is a schematic depiction of a non-invasive analyte sensor system with an analyte sensor relative to a target according to an embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The following is a detailed description of apparatus, systems and methods of detecting an analyte via spectroscopic techniques using non-optical frequencies such as in the radio or microwave frequency bands of the electromagnetic spectrum. An analyte sensor described herein includes a plurality of antennas or detector elements, at least one of which can transmit an electromagnetic signal in the radio or microwave frequency range into a target and at least one of which can receive an electromagnetic signal in the radio or microwave frequency range resulting from transmission of the electromagnetic signal. In an embodiment, the antennas may be part of a common antenna array. Further information on the construction and operation of analyte sensors that use radio or microwave frequency bands of the electromagnetic spectrum for collection of analyte data are disclosed in WO 2019/217461, U.S. Pat. Nos. 11,063,373, 11,058,331, 11,033,208, 11,284,819, 11,284,820, 10,548,503, 11,234,619, 11,031,970, 11,223,383, 11,058,317, 11,193,923, 11,234,618, 11,389,091, U.S. 2021/0259571, U.S. 2022/0077918, U.S. 2022/0071527, U.S. 2022/0074870, U.S. 2022/0151553, each of which is incorporated herein by reference in its entirety.

Health care assessment or medical diagnostics can be performed via an apparatus or article which is non-invasive, non-intrusive, and, or which monitors health on a periodic basis one or more times a day, and even on an hourly, or minute-by-minute basis, or even continuously or near-continuously, and which can provide real time or almost real time results. In at least some implementations, an interface is worn by a subject in an unobtrusive manner, for example as a band worn around a portion of an appendage. The interface includes one or more antennas to transmit excitations signals through adjacently located bodily tissue, and to receive response signals and compare these response signals to the excitation signals after they pass through the bodily tissue. The excitation signals and the response signals are preferably in non-optical (i.e., outside the visible, infrared, ultraviolet bands) portions or bands of the electromagnetic spectrum, for instance the radio and, or microwave frequency bands of the electromagnetic spectrum.

Since such medical diagnostic systems use antennas having response and excitation signals in non-optical portions of the electromagnetic spectrum, not only can such diagnostic systems generate electromagnetic interference which could adversely affect any external medical equipment, especially in a hospital environment, the antennas may receive electromagnetic interference, e.g., from external sources or other components of the diagnostic system or reflections therefrom, which may lead to inaccurate measurements of the analyte in the target.

For example, the FDA has provided a Guidance for Industry and Food and Drug Administration Staff entitled "Radio Frequency Wireless Technology in Medical Devices" issued Aug. 14, 2013 (https://www.fda.gov/media/71975/download). In the Guidance, the FDA has indicated that potential interference exists for medical (ISM) frequency bands (e.g., 2400-2493.5 MHz), because this frequency band is already heavily used by many other communications and industrial products. The FDA recommends in the Guidance that the following factors be considered during the device design and development of medical devices:

1) Electromagnetic disturbance (EMD)—any electromagnetic phenomenon that might degrade the performance of an equipment, such as medical devices or any electronic equipment. Examples include power line voltage dips and interruptions, electrical fast transients (EFTs), electromagnetic fields (radio frequency radiated emissions), electrostatic discharges, and conducted emissions.
2) Electromagnetic interference (EMI)—degradation of the performance of a piece of equipment, transmission channel, or system (such as medical devices) caused by an electromagnetic disturbance.
3) Emissions—electromagnetic energy emanating from a device generally falling into two categories: conducted and radiated. Both categories of emission can occur simultaneously, depending on the configuration of the device.
4) Conducted emissions—electromagnetic energy emanating from a product through a conductor by means of resistance, inductance, or capacitance. Conductors include AC power cords, metallic enclosures of a subsystem, or cables that interconnect subsystems or the patient to the product. Conducted emissions include power line harmonics, surges, and radio frequency energy, especially in the frequency range 150 kHz to 80 MHz.
5) Radiated emissions—electromagnetic energy emanating from a device and propagating through space or a medium (which can affect the distance and direction of propagation). Radiated emissions include both intentional emissions such as radio transmissions carrying information and unintentional emissions associated with electrically powered equipment such as motors, power supplies, and computer components.

Additionally, there has been increased reports of electromagnetic interference, e.g., RF interference, to devices such as ventilators, patient monitors, pacemakers, neonatal infant warmers, motorized wheelchairs, and anesthesia delivery equipment, or the like, in hospital settings. Effects of the interference varied from false alarms and indications to unwanted mode and operational changes and incorrect operations.

The following is a detailed description of apparatus, systems and methods of detecting an analyte via spectroscopic techniques using non-optical frequencies such as in the radio or microwave frequency bands of the electromagnetic spectrum that overcomes the deficiencies of prior medical diagnostic systems. In an embodiment, a non-invasive analyte sensor described herein that can be used to perform in vivo diagnostics may include a first antenna, which can include a plurality of antennas (also referred to as antenna elements); at least a second antenna, which can include a plurality of antennas, the second antenna spaced laterally with respect to the first antenna by a first range of distances that provide for near field communications between the first and the second antennas, at least one of which can transmit an electromagnetic signal in the radio or microwave frequency range and at least one of which can receive an electromagnetic signal in the radio or microwave frequency range resulting from transmission of the electromagnetic signal; and at least one electromagnetic force (EMF) shield, also referred to as an electromagnetic shield, positioned with respect to the first and the second antennas that provides a communicative path for the first and the second antennas in a first direction, e.g., propagating direction, through a mounting interface that in use is proximally adjacent the bodily tissue or target and that mostly electromagnetically isolates the second antenna from direct communications with the first antenna except along a path that passes through the bodily tissue or target. In another embodiment, the EMF shield at least partially electromagnetically isolates at least one component of the analyte sensor to at least partially electromagnetically isolate the at least one component from RF interference and/or MF interference. The at least one EMF shield may be a sheet of a metal foil or a conductive paint and/or coating, e.g., a conductive spray coating on a component or part.

In one embodiment, the analyte sensor described herein can be used to detect the presence of at least one analyte in a target. In another embodiment, the analyte sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, one or more of blood, interstitial fluid, cerebral spinal fluid, lymph fluid or urine, human tissue, animal tissue, plant tissue, an inanimate object, soil, genetic material, or a microbe.

The excitations signals are generated via one or more transmitters or transmit circuits, operable to generate and provide excitation signals at each of a plurality of discrete frequencies over a set or a plurality of frequencies, for instance from 300 MHz to 2500 MHz. The response signals are received via one or more receivers or receive circuits that is operable to receive signals at each of a plurality of discrete frequencies over a set of a plurality of frequencies, for instance from 300 MHz to 2500 MHz or between 300 MHz and 2000 MHz.

The signal(s) detected by the receive antenna can be analyzed to detect the analyte based on the intensity of the received signal(s) and reductions in intensity at one or more frequencies where the analyte absorbs the transmitted signal and/or reflection or refraction of the signal. An example of detecting an analyte using a non-invasive spectroscopy sensor operating in the radio or microwave frequency range of the electromagnetic spectrum is described in U.S. Pat. No. 10,548,503, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

The non-invasive analyte sensor system, for example a processor-based system, can also be operable to determine differences between the response signals and the respective excitation signals that gave rise to the respective response signals. Thus, the processor-based system is operable to assess signals such as S parameters and/or transition line parameters and/or dielectric parameters. An example being the amount of gain or loss (e.g., dB) between the excitation signals and the corresponding response signals which results from passage of the signals through at least a portion of bodily tissue that is being assessed or sampled, e.g., a target. At least some of these determined differences are the result of, and hence characterize, one or more physical conditions or states of the bodily tissue or concentrations of material within the bodily tissue at the time of the assessment or performance of the medical diagnostics, referred to herein as sampling.

The non-invasive analyte sensor system can compare the determined differences to a set of baseline determined differences, collected at a previous time, and which characterize one or more physical conditions or states of the bodily tissue at a baseline state, for example producing a set of differences between the current state values and the baseline state values. The baseline state may represent a healthy state, or may simply represent a starting state, whether the subject is considered healthy at that time or not. The baseline state may represent a baseline for the particular subject being assessed, or may represent a generic baseline common across many subjects. The non-invasive analyte sensor system may compare a difference between one or more of the sampling state values (e.g., differences between the excitation and response signals captured at a current or sampling time) and one or more of the baseline state values (e.g., differences between the excitation and response signals captured at a baseline time). The non-invasive analyte sensor system may assess whether a defined pattern exists or is absent from the differences, and provide an indication of a presence or absence of an anomalous physical condition or other difference or null difference of the subject based on the comparison identified.

The transmit antenna and the receive antenna may be decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The detection by the sensors described herein can be non-invasive meaning that the sensor remains outside the target, such as the human body, and the detection of the analyte occurs without requiring removal of fluid or other removal from the target, such as the human body. In the case of sensing in the human body, this non-invasive sensing may also be referred to as in vivo sensing. In other embodiments, the sensors described herein may be an in vitro sensor where the material containing the analyte has been removed, for example from a human body.

The analyte(s) can be any analyte that one may wish to detect. The analyte can be human or non-human, animal or non-animal, biological or non-biological. For example, the analyte(s) can include, but is not limited to, one or more of glucose, blood alcohol, oxygen or an indicator thereof, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. In an embodiment, the analyte may be simultaneously detected from both blood and interstitial fluid. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin and variants thereof including hemoglobin A, hemoglobin S, hemoglobin C, hemoglobin D, hemoglobin E, hemoglobin F, D-Punjab, and beta-thalassemia, particular conformations or conjugations of hemoglobin such as oxyhemoglobin, deoxyhemoglobin, carboxyhemoglobin, and the like; hepatitis B virus; HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants;

hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; zinc protoporphyrin; prostaglandins such as PGF2α and PGE2; hormones such as estrogen, progesterone, and/or follicle stimulating hormone (FSH).

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol or other alcohols; ketones; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

In an embodiment, the analyte(s) are one or more analytes that can be used to determine an oxygen level in a subject. The analytes can be, for example, elemental oxygen, oxyhemoglobin, deoxyhemoglobin, or any other suitable analyte indicative of or a proxy for the oxygen level in the subject. The oxygen level can be an overall level of oxygen or analyte(s) indicative of or a proxy for oxygen by itself, or can be a ratio such as a ratio of oxyhemoglobin to deoxyhemoglobin.

In an embodiment, the analyte(s) can include one or more indicators for determination of hydration of a subject. The analyte(s) can include, for example, hemoglobin, red blood cells as a whole, one or more hormones, sodium, one or more solutes from which osmolarity can be determined, or the like. The amount of the analyte(s) can be used to determine one or more indicia of hydration, such as concentrations of one or more analytes, hematocrit, osmolarity, or any other suitable measurement of a hydration level of the subject. The osmolarity can be an osmolarity of one or more of plasma, interstitial fluid, saliva, urine, or the like. In an embodiment, a sensor can be positioned such that the results of detection are indicative of the presence or amount of analytes in the bladder of the subject, such that urine parameters related to hydration such as urine osmolarity can be determined. In an embodiment, the sensor can be positioned such that results of detection are indicative of the presence or amount of analytes in saliva. A hydration level can be determined based on the one or more indicators, for example by comparing osmolarity or hematocrit to reference values. The reference values can be reference values specific to the subject, general reference values, reference values for a group that the subject belongs to, or the like. In an embodiment, the sensor can detect the one or more analytes in the subject non-invasively. In an embodiment, the sensor can detect the one or more analytes in a sample obtained from the subject, such as a blood, urine, or saliva sample. The sample can have a predetermined mass or volume.

In an embodiment, the sensor described herein can be incorporated into a wearable device such as a ring, a watch, or any other suitable wearable device that is worn on the user's body. The wearable device may be configured to be worn by the user over a longer period of time, for example a watch, a ring, or the like. Alternatively, the wearable device may be configured to be temporarily worn, for example only during one or more analyte readings after which the wearable device is removed. In an embodiment, the sensor described herein can be configured as a non-wearable device. For example, the sensor can be configured as a device that a user holds or presses against a body part during an analyte reading, or a body part is pressed against the sensor, during an analyte reading.

The device including the sensor, whether wearable or non-wearable, can also be configured to be capable of detecting one or more physiological parameters such as user heart rate, user blood pressure, user body temperature, user calorie consumption, user glucose level, one or more hormone levels, bioelectric impedance, or the like. One or more of the physiological parameters can be detected directly using the sensor and/or determined based on detection of one or more analytes by the sensor. In an embodiment, one or more of the physiological parameters can be detected or determined using one or more additional physiological sensors included in the device in addition to the sensor described herein. The one or more additional physiological sensors can be any suitable physiological sensor for the particular physiological parameter to be sensed. In an embodiment, one or more of the physiological parameters can be determined based on a presence or amount of one or more analytes detected by the sensor and one or more additional measurements made by one or more additional physiological sensors included in the device. The device can also include one or more additional functionalities including, but not limited to, a camera; an accelerometer; a pedometer; a fitness/activity tracker; an altimeter; a barometer; a compass; a global positioning system; a sleep monitor; a fall sensor; a microphone; a speaker; and others.

FIG. 1 illustrates an embodiment of a non-invasive analyte sensor system 100 to perform health assessments or diagnostics on bodily tissue. The non-invasive analyte sensor system 100 can include an interface 104 that comprises one or more antennas 106a, 106b (two shown, collectively 106) to couple excitation signals to bodily tissue, e.g., a target, and to receive response signals therefrom. The non-invasive analyte sensor system 100 may include one or more transmitters 108 and one or more receivers 110 which are communicatively coupled to drive the antennas 106 to emit the excitation signals and to detect or receive the response signals. The non-invasive analyte sensor system 100 may include one or more processor-based devices or systems 112, communicatively coupled to the receiver 110 and optionally communicatively coupled to the transmitter 108, and operable to analyze the response signals returned from the body. The processor-based device or system 112 may include, or be communicatively coupled to an indicator 114, for example a visual indication (e.g., light emitting diode(s), liquid crystal display (LCD), or other visual display device), or to an aural or haptic indication (e.g., speaker, buzzer), and/or to an external device such as a user device and/or a remote server, for example through one or more wireless connections such as Bluetooth, wireless data connections such a 4G, 5G, LTE or the like, or Wi-Fi. If provided, the external device and/or remote server may process (or further process) the signals that the controller receives from the receive circuit, for example to detect the analyte(s).

The non-invasive analyte sensor system 100, or components thereof (e.g., interface 104) may take any of a variety of forms, for example a system or device used in a clinical or hospital setting, although preferably one or more components take the form of a wearable device that can be unobtrusively worn by an individual for instance during normal, everyday routines. For example, in some implementations the interface 104 with the antennas 106, transmitter 108, receiver 110, and processor-based device or system 112 are all packaged together as a single integral wearable device (e.g., smartwatch, band, cuff, ring, neckless, earrings, or fitness tracker). In other implementations, the interface 104 with the antennas 106, transmitter 108, and receiver 110, are all packaged together as a single integral wearable device (e.g., smartwatch, band, cuff, ring, neckless, earrings, or fitness tracker), and the processor-based device or system 112 is separate or distinct from the single integral wearable device. The separate or distinct processor-based device or system 112 may, for example, take the form of a smartphone, a processor enabled device, or a tablet computer that is proximate the interface, transmitter and receiver in use, for example within range of a Bluetooth radio and antenna. The separate or distinct processor-based device or system 112 may, for example, take the form of remotely located computer system (e.g., server computer, back end computer system) that is remote from the single integral wearable device, for example at a fixed location, and communicatively coupled via one or more network infrastructures. In such implementations, the single integral wearable device can communicate with the separate or distinct processor-based device or system 112 via any variety of wired and/or wireless communications infrastructures, for instance radios (e.g., WI-FI radios, cellular radios), base stations, the Internet, etc. Other forms of wireless, optical (e.g., infrared) or even wired communications may be employed.

The interface 104 may be as simple as two antennas 106, or may include a housing or other structure that spaces one of the antennas 106b laterally from the other one of the antennas 106a. The lateral spacing may, for example be 1 mm inclusive to 2 mm inclusive, although the antennas 106a, 106b may be spaced further apart (e.g., 1 mm to 20 mm), but within a distance in which near field communications occur between the antennas 106a, 106b via the bodily tissue or target. The interface 104 may be shaped and sized to position the antennas 106a, 106b adjacent or proximate to the bodily tissue or target, for example close to, but not in contact with the bodily tissue or target. While illustrated as a forearm, wrist and hand, the bodily tissue or target can take the form of any other portion of bodily tissue, for example the earlobe or abdomen.

As discussed in detail below, the interface 104 may include the antennas 106 and an optional shield (e.g., EMF shield) 116 that prevents or substantially (e.g., equal to or greater than 30 dB reduction) limits wireless communications (e.g., communications in the radio frequency band and/or microwave frequency band) directly between the antennas 106a, 106b, causing near field wireless communications between the antennas 106a, 106b to pass at least partially through the bodily tissue or target. As described herein, the shield 116 can take a variety of forms, for example an electrically conductive material, for instance a metal, and can passively or actively provide the electromagnetic shielding. The electromagnetic shield 116 may, for example, include stainless steel, conductive polymers, e.g., a nanocomposite, or more preferably a metal foil (e.g. aluminum foil, copper foil), or a metalized flexible substrate, for instance a metalized Mylar™, metalized paper polyethylene, metalized plastic laminate, cardboard, fiberboard, conductively filled paint or coating, etc., that have high conductivity, dielectric constant, or high magnetic permeability. The metal acts as a shield (e.g., partial Faraday cage). The electromagnetic shield 116 may, for example, include a metal sheet or foil, a wire metal mesh, metal coated film, or printed circuit board with a metal layer and/or that can be electrically activated. A large variety of metals may be suitable, e.g., copper, aluminum. A large variety of thicknesses may be suitable. The electromagnetic shield 116 should have sufficient dimensions (e.g., length, width, thickness, diameter, circumference) to ensure that the response signals are received via at least one of the antennas (e.g., receiving antenna) 106.

Various structures are referred to as shielded, that is shielded at least from certain radio frequencies or wavelengths and/or microwave frequencies or wavelengths in the frequency ranges or wavelength ranges at which the non-invasive analyte sensor system operate, i.e., frequency ranges or wavelength ranges of excitation signals transmitted by the transmitters and/or frequency ranges or wavelength ranges of response signals received by the receivers. The shield may be a Faraday cage or partial Faraday cage, that sufficiently attenuates electromagnetic signals as to prevent communications directly between the antennas 106 without passing at least partially through the bodily tissue. The shield can comprise sheets and/or meshes of conductive material (e.g., aluminum, copper, silver, gold, mild steel), of sufficient conductivity, thickness, and geometry as to cause attenuation (e.g., 30 dB, 50 dB; 60 dB reduction via a silver coated nylon fabric; 85 dB reduction via aluminum foil, 120 dB reduction via Mu-copper foil of 0.12 mm thick) in the particular wavelength or frequency ranges of interest (e.g., 350 MHz-2500 MHz). Where a mesh is employed, the holes or apertures of the mesh should have a characteristic dimension that is much smaller (e.g., ¼ wavelength) than the wavelength of the signal to be stopped (i.e., excitation signal and/or response signal). In other embodiments, the EMF shielding at least partially electromagnetically isolates at least one electrical component of the non-invasive analyte sensor system. In an embodiment, the EMF shielding partially electromagnetically isolates the at least one electrical component, for example, by allowing the antenna(s) to propagate the radio frequency electromagnetic waves or the magnetic frequency electromagnetic waves in the propagating direction, e.g., towards the bodily tissue, but shields the remaining components of the non-invasive analyte sensor system 100 (and any external devices) from the radio frequency electromagnetic waves and/or the magnetic frequency electromagnetic waves and/or shields the antenna(s) and/or the transmitting/receiving module from any radio frequency electromagnetic waves and/or the magnetic frequency electromagnetic waves from external sources, e.g., pacemakers, apnea monitors, electrically powered wheelchairs, monitors, etc. In another embodiment, the EMF shielding electromagnetically isolates at least one of the electrical components of the non-invasive analyte sensor system, from exterior sources of radio frequency and/or magnetic frequency noise, and/or to prevent and/or mitigate the transmission of the radio frequency electromagnetic waves or the magnetic frequency electromagnetic waves from being transmitted or emitted in a direction other than the propagating direction, e.g., towards the other components of the non-invasive analyte sensor system 100. While the embodiments discussed herein relate to the non-invasive analyte sensor system and components therein, it is understood that the EMF shielding can also be provided on the wires, cables, connectors, or components external to the non-invasive analyte sensor system to electromagnetically isolate the same from radio frequency interference and/or microwave frequency interference (from receiving or transmitting interfering radio frequency electromagnetic waves and/or magnetic frequency electromagnetic waves), e.g., power cables or wires connected to an external processor-based device. As used herein, the EMF shielding is configured to reduce noise and/or interfering or stray EMF signals, e.g., from reflections, outside signals, or from internal components, by at least 90%, 95%, 98%, or 99%.

Figure 2A:
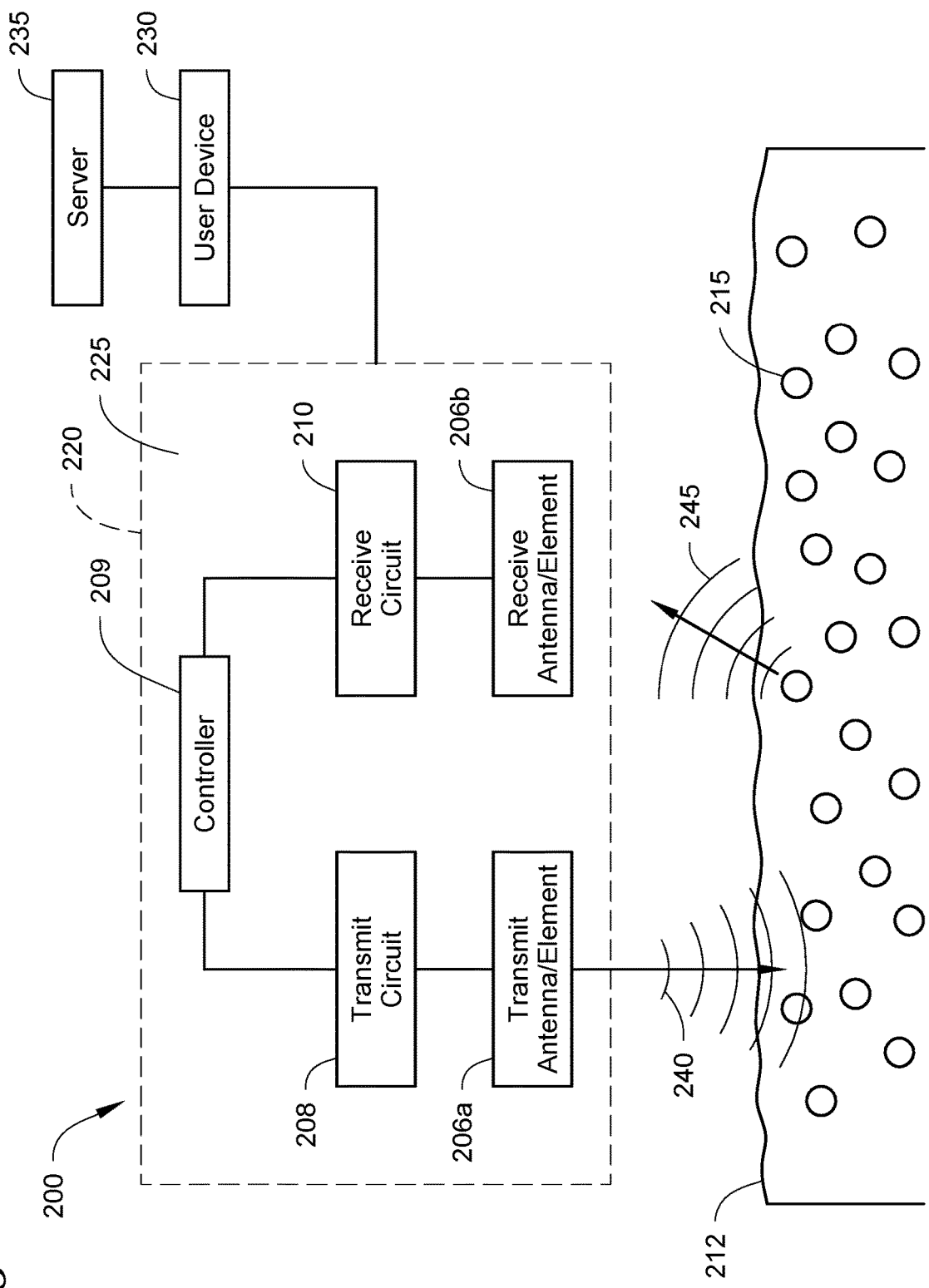
FIG. 2A is a schematic depiction of a non-invasive analyte sensor system with an analyte sensor relative to a target according to another embodiment.

FIG. 2A illustrates another embodiment of a non-invasive analyte sensor system with a non-invasive analyte sensor 200. The sensor 200 is depicted relative to a target 212 that contains an analyte of interest 215, for example an analyte in interstitial fluid in a human body. In this example, the sensor 200 is depicted as including an antenna array that includes a transmit antenna/element 206a (hereinafter "transmit antenna 206a") and a receive antenna/element 206b (hereinafter "receive antenna 206b"). The sensor 200 further includes a transmit circuit 208, a receive circuit 210, and a controller 209. As discussed further below, the sensor 200 can also include a power supply, such as a battery (not shown in FIG. 2A). In some embodiments, power can be provided from mains power, for example by plugging the sensor 200 into a wall socket via a cord connected to the sensor 200.

The transmit antenna 206a is positioned, arranged and configured to transmit a signal 240 that is the radio frequency (RF) or microwave frequency (MF) range of the electromagnetic spectrum into the target 212. The transmit antenna 206a can be an electrode or any other suitable transmitter of electromagnetic signals in the RF or MF range. The transmit antenna 206a can have any arrangement and orientation relative to the target 212 that is sufficient to allow the analyte sensing to take place. In one non-limiting embodiment, the transmit antenna 206a can be arranged to face in a direction that is substantially toward the target 212, including but not limited to close to, but not in contact with the target 212.

The signal 240 transmitted by the transmit antenna 206a is generated by the transmit circuit 208 which is electrically connectable to the transmit antenna 206a. The transmit circuit 208 can have any configuration that is suitable to generate a transmit signal to be transmitted by the transmit antenna 206a. In one embodiment, the transmit circuit 208 can include, for example, a connection to a power source, a frequency generator, and optionally filters, amplifiers or any other suitable elements for a circuit generating an RF or microwave frequency electromagnetic signal. In an embodiment, the signal generated by the transmit circuit 208 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the signal can be a single signal generated by the transmit circuit 208 can be in the range from about 300 MHz to about 6000 MHz or 300 MHz to about 2000 MHz. In an embodiment, the transmit circuit 208 can be configured to sweep through a range of frequencies that are within the range of about 10 kHz to about 100 GHz, or in another embodiment a range of about 300 MHz to about 6000 MHz. In an embodiment, the transmit circuit 208 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 206b is positioned, arranged, and configured to detect one or more electromagnetic response signals 245 that result from the transmission of the transmit signal 240 by the transmit antenna 206a into the target 212 and impinging on the analyte 215. The receive antenna 206b can be an electrode or any other suitable receiver of electromagnetic signals in the RF or MF range. In an embodiment, the receive antenna 206b is configured to detect electromagnetic signals having at least two frequencies, each of which is in the range from about 10 kHz to about 100 GHz, or in another embodiment a range from about 300 MHz to about 6000 MHz or 300 MHz to about 2000 MHz. In an embodiment, the signal can be a single signal received by the receive circuit 210 in the range from about 300 MHz to about 6000 MHz or 300 MHz to about 2000 MHz. The receive antenna 206b can have any arrangement and orientation relative to the target 212 that is sufficient to allow detection of the response signal(s) 245 to allow the analyte sensing to take place. In one non-limiting embodiment, the receive antenna 206b can be arranged to face in a direction that is substantially toward the target 212, including but not limited to close to, but not in contact with the target 212.

The receive circuit 210 is electrically connectable to the receive antenna 206b and conveys the received response from the receive antenna 206b to the controller 209. The receive circuit 210 can have any configuration that is suitable for interfacing with the receive antenna 206b to convert the electromagnetic energy detected by the receive antenna 206b into one or more signals reflective of the response signal(s) 245. The receive circuit 210 can be configured to condition the signal(s) prior to providing the signal(s) to the controller 209, for example through amplifying the signal(s), filtering the signal(s), or the like. Accordingly, the receive circuit 210 may include filters, amplifiers, or any other suitable components for conditioning the signal(s) provided to the controller 209. In an embodiment, at least one of the receive circuit 210 or the controller 209 can be configured to decompose or demultiplex a complex signal, detected by the receive antenna 206b, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

It is appreciated that the term "electrically connectable" includes but is not limited to the circuit being electrically connected to the respective antenna, e.g., conductive trace, wires, switches, or the like. In an embodiment, a switching circuit can be used to selectively connect the transmit circuit 208 or receive circuit 210 to different antennas for transmitting or receiving the transmit signal 240 or response signal 245. As such, the non-invasive analyte sensor system can be selectively adjusted for various sensing positions and/or response positions e.g., based on the target and/or analyte for detection.

The controller 209 controls the operation of the sensor 200. The controller 209, for example, can direct the transmit circuit 208 to generate a transmit signal to be transmitted by the transmit antenna 206a. The controller 209 further receives signals from the receive circuit 210. The controller 209 can optionally process the signals from the receive circuit 210 to detect the analyte(s) 215 in the target 212. In one embodiment, the controller 209 may optionally be in communication with at least one external device 230 such as a user device and/or a remote server 235, for example through one or more wireless connections such as Bluetooth, wireless data connections such a 4G, 5G, LTE or the like, or Wi-Fi. If provided, the external device 230 and/or remote server 235 may process (or further process) the signals that the controller 209 receives from the receive circuit 210, for example to detect the analyte(s) 215. If provided, the external device 230 may be used to provide communication between the sensor 200 and the remote server 235, for example using a wired data connection or via a wireless data connection or Wi-Fi of the external device 2302 to provide the connection to the remote server 235.

As further seen in FIG. 2A, the sensor 200 may include a sensor housing 220 (shown in dashed lines) that defines an interior space 225. Components of the sensor 200 may be attached to and/or disposed within the housing 220. For example, the transmit antenna 206a and the receive antenna 206b are attached to the housing 220 (or internal thereto spaced apart from the housing). In some embodiments, the antennas 206a, 206b may be entirely or partially within the interior space 225 of the housing 220. In some embodiments, the antennas 206a, 206b may be attached to the housing 220 but at least partially or fully located outside the interior space 225. In some embodiments, the transmit circuit 208, the receive circuit 210, and the controller 209 are attached to the housing 220 and disposed entirely within the sensor housing 220.

The receive antenna 206b may be decoupled or detuned with respect to the transmit antenna 206a such that electromagnetic coupling between the transmit antenna 206a and the receive antenna 206b is reduced. The decoupling of the transmit antenna 206a and the receive antenna 206b increases the portion of the signal(s) detected by the receive antenna 206b that is the response signal(s) 245 from the target 212, and minimizes direct receipt of the transmitted signal 240 by the receive antenna 206b. The decoupling of the transmit antenna 206a and the receive antenna 206b results in transmission from the transmit antenna 206a to the receive antenna 206b having a reduced forward gain (S21) and an increased reflection at output (S22) compared to antenna systems having coupled transmit and receive antennas.

In an embodiment, coupling between the transmit antenna 206a and the receive antenna 206b is 95% or less. In another embodiment, coupling between the transmit antenna 206a and the receive antenna 206b is 90% or less. In another embodiment, coupling between the transmit antenna 206a and the receive antenna 206b is 85% or less. In another embodiment, coupling between the transmit antenna 206a and the receive antenna 206b is 75% or less.

In one embodiment, the transmit signal that is transmitted by the transmit antenna 206a can have at least two different frequencies, for example upwards of 7 to 12 different and discrete frequencies. In another embodiment, the transmit signal can be a series of discrete, separate signals with each separate signal having a single frequency or multiple different frequencies.

Any technique for reducing coupling between the transmit antenna 206a and the receive antenna 206b can be used. For example, the decoupling between the transmit antenna 206a and the receive antenna 206b can be achieved by one or more intentionally fabricated configurations and/or arrangements between the transmit antenna 206a and the receive antenna 206b that is sufficient to decouple the transmit antenna 206a and the receive antenna 206b from one another.

For example, in one embodiment described further below, the decoupling of the transmit antenna 206a and the receive antenna 206b can be achieved by intentionally configuring the transmit antenna 206a and the receive antenna 206b to have different geometries from one another. Intentionally different geometries refers to different geometric configurations of the transmit and receive antennas 206a, 206b that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 206a and the receive antenna 206b is to provide appropriate spacing between each antenna 206a, 206b that is sufficient to decouple the antennas 206a, 206b and force a proportion of the electromagnetic lines of force of the transmitted signal 240 into the target 212 thereby minimizing or eliminating as much as possible direct receipt of electromagnetic energy by the receive antenna 206b directly from the transmit antenna 206a without traveling into the target 212. The appropriate spacing between each antenna 206a, 206b can be determined based upon factors that include, but are not limited to, the output power of the signal from the transmit antenna 206a, the size of the antennas 206a, 206b, the frequency or frequencies of the transmitted signal, and the presence of any shielding between the antennas. This technique helps to ensure that the response detected by the receive antenna 206b is measuring the analyte of interest 215 and is not just the transmitted signal 240 flowing directly from the transmit antenna 206a to the receive antenna 206b. In some embodiments, the appropriate spacing between the antennas 206a, 206b can be used together with the intentional difference in geometries of the antennas 206a, 206b to achieve decoupling.

In one embodiment, the transmit signal (or each of the transmit signals) can be transmitted over a transmit time that is less than, equal to, or greater than about 300 ms. In another embodiment, the transmit time can be less than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

As mentioned above, one technique for decoupling the transmit antenna 206a from the receive antenna 206b is to intentionally configure the transmit antenna 206a and the receive antenna 206b to have intentionally different geometries. The different geometries of the antennas 206a, 206b may manifest itself, and may be described, in a number of different ways. For example, in a plan view of each of the antennas 206a, 206b (such as in FIGS. 2B-D), the shapes of the perimeter edges of the antennas 206a, 206b may be different from one another. The different geometries may result in the antennas 206a, 206b having different surface areas in plan view. The different geometries may result in the antennas 206a, 206b having different aspect ratios in plan view (i.e. a ratio of their sizes in different dimensions; for example, as discussed in further detail below, the ratio of the length divided by the width of the antenna 206a may be different than the ratio of the length divided by the width for the antenna 206b). In some embodiments, the different geometries may result in the antennas 206a, 206b having any combination of different perimeter edge shapes in plan view, different surface areas in plan view, and/or different aspect ratios.

So as used herein, a difference in geometry or a difference in geometrical shape of the antennas 206a, 206b refers to any intentional difference in the figure, length, width, size, shape, area closed by a boundary (i.e. the perimeter edge), etc. when the respective antenna 206a, 206b is viewed in a plan view.

The antennas 206a, 206b can have any configuration and can be formed from any suitable material that allows them to perform the functions of the antennas 206a, 206b as described herein. In one embodiment, the antennas 206a, 206b can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 2B-D). A strip of material can include a wire. In an embodiment, the antennas can be curved. The antennas 206a, 206b can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive. In an embodiment, the antennas can be covered with soldermask with a via to the bottom side where an RF connector and ground plane are located. In an embodiment, a dielectric, such as FR4, can be used to load any gaps between components.

Figure 2B:
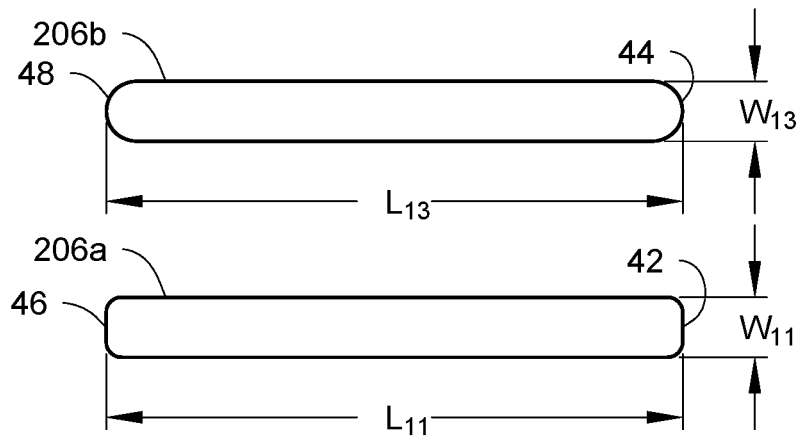
FIGS. 2B-2D illustrate different examples of transmit and receive antennas with different geometries.

FIG. 2B illustrates a plan view of an antenna array having two antennas with different geometries. In this example, the antennas 206a, 206b are illustrated as substantially linear strips. In this example, the antennas 206a, 206b differ in geometry from one another in that the shapes of the ends of the antennas 206a, 206b differ from one another. For example, when viewing FIG. 2B, the right end 42 of the antenna 206a has a different shape than the right end 44 of the antenna 206b. Similarly, the left end 46 of the antenna 206a may have a similar shape as the right end 42, but differs from the left end 48 of the antenna 206b which may have a similar shape as the right end 44. It is also possible that the lateral lengths $L_{11}$, $L_{13}$ and/or the lateral widths $W_{11}$, $W_{13}$ of the antennas 206a, 206b could differ from one another.

Figure 2C:
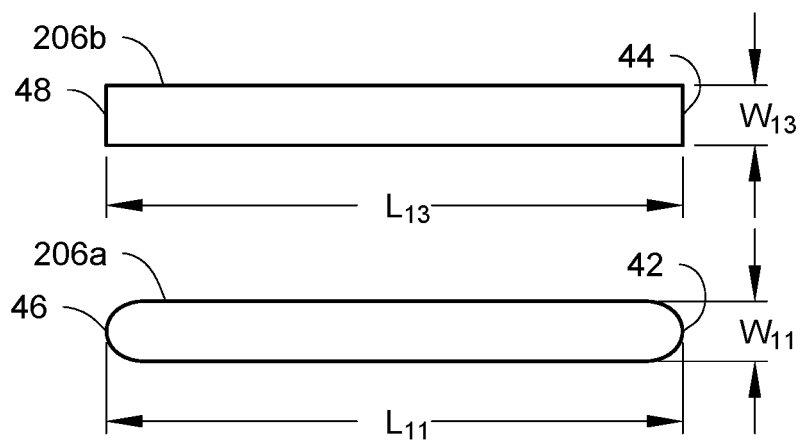

FIG. 2C illustrates another plan view of an antenna array having two antennas with different geometries that is somewhat similar to FIG. 2B. In this example, the antennas 206a, 206b are illustrated as substantially linear strips, and the antennas 206a, 206b differ in geometry from one another in that the shapes of the ends of the antennas 206a, 206b differ from one another. For example, when viewing FIG. 2C, the right end 42 of the antenna 206a has a different shape than the right end 44 of the antenna 206b. Similarly, the left end 46 of the antenna 206a may have a similar shape as the right end 42, but differs from the left end 48 of the antenna 206b which may have a similar shape as the right end 44. In addition, the lateral widths $W_{11}$, $W_{13}$ of the antennas 206a, 206b differ from one another. It is also possible that the lateral lengths $L_{11}$, $L_{13}$ of the antennas 206a, 206b could differ from one another.

Figure 2D:
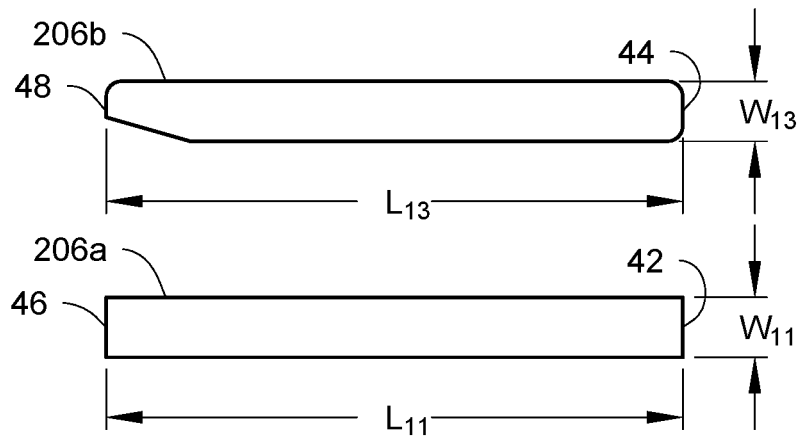

FIG. 2D illustrates another plan view of an antenna array having two antennas with different geometries that is somewhat similar to FIGS. 2B and 2C. In this example, the antennas 206a, 206b are illustrated as substantially linear strips, and the antennas 206a, 206b differ in geometry from one another in that the shapes of the ends of the antennas 206a, 206b differ from one another. For example, when viewing FIG. 2D, the right end 42 of the antenna 206a has a different shape than the right end 44 of the antenna 206b. Similarly, the left end 46 of the antenna 206a may have a similar shape as the right end 42, but differs from the left end 48 of the antenna 206b which may have a similar shape as the right end 44. In addition, the lateral widths $W_{11}$, $W_{13}$ of the antennas 206a, 206b differ from one another. It is also possible that the lateral lengths $L_{11}$, $L_{13}$ of the antennas 206a, 206b could differ from one another.

While the antenna array has been discussed above with respect to different geometries at the ends of the antennas, such disclosure is not intended to be limiting, but rather provide disclosure of different antenna geometries can be used. For example, in an embodiment, the antenna array can have two antennas that have a first longitudinal length and a first width that is smaller than the first longitudinal length, e.g., a long (rectangular) electrode. In another embodiment, the antenna array can have two antennas that have a second longitudinal length and a second width that is smaller than the second longitudinal length, in which the second longitudinal length is smaller than the first longitudinal length, e.g., short electrode. In an embodiment, the antenna array can include a combination of the short electrodes sandwiched with the long electrode.

The interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

Referring to FIG. 3, an embodiment of a non-invasive analyte sensor system 300 is schematically illustrated to discuss components of the sensor 300, in which the EMF shield is not illustrated. The sensor 300 is similar to the sensors 100, 200 in FIGS. 1, 2 discussed above and can include the same or similar elements, which are not discussed in detail below. In this embodiment, the sensor 300 is depicted as including an antenna array that includes a plurality of transmit antennas 306a (which can include a single antenna or two or more antennas) and a plurality of receive antennas 306b (which can include a single antenna or two or more antennas) that are carried by a substrate 350 which are enclosed by a housing 320. The sensor 300 further includes a transmit circuit 308, a receive circuit 310, and a controller, which can be mounted on the substrate 350. As discussed further below, the sensor 300 can also include a power supply 360, such as a battery. In some embodiments, power can be provided from mains power, for example by plugging the sensor 300 into a wall socket via a cord connected to the sensor 300.

The transmit antennas 306a are positioned, arranged and configured to transmit a signal that is in the RF or MF range of the electromagnetic spectrum into a target. The transmit antennas 306a can be an electrode or any other suitable transmitter of electromagnetic signals in the radio frequency (RF) or microwave range. The transmit antennas 306a can have any arrangement and orientation relative to the target that is sufficient to allow the analyte sensing to take place. In one non-limiting embodiment, the transmit antennas 306a can be arranged to face in a direction that is substantially toward the target, including but not limited to close to, but not in contact with the target.

The receive antennas 306b are positioned, arranged, and configured to detect one or more electromagnetic response signals that result from the transmission of the transmit signal by the transmit antenna 306a into the target and impinging on the analyte. The receive antennas 306b can be an electrode or any other suitable receiver of electromagnetic signals in the RF or MF range. The receive antennas 306b can have any arrangement and orientation relative to the target that is sufficient to allow detection of the response signal(s) to allow the analyte sensing to take place. In one non-limiting embodiment, the receive antennas 306b can be arranged to face in a direction that is substantially toward the target, including but not limited to close to, but not in contact with the target.

It is appreciated that the antennas 306a, 306b can be selectively electrically connectable to either the transmit circuit 308 or the receive circuit 310. In an embodiment, a switching circuit can be used for selectively connecting the transmit circuit 308 or receive circuit 310 to the different antennas for transmitting or receiving the transmit signal or response signal. As such, the non-invasive analyte sensor system can be selectively adjusted for various sensing positions or response positions e.g., based on the target and/or analyte for detection.

The antennas 306a, 306b can be mounted to or connected to the substrate 350 by any known technique, for example, soldering, bump arrays, flip chip fashion, conductive tracks, cables, wires, pinned connection, etc. for electrically connecting the antennas 306a, 306b to the substrate 350. In an embodiment, the transmit circuit 308 and the receive circuit 310 are mounted on the substrate 350 by any of the known techniques. The transmit antenna 306a is electrically connected to the transmit circuit 308 via an electrical conductor 311 (which may be also be referred to as a cable or wire) and the receive antenna 306b is electrically connected to the receive circuit 310 via an electrical conductor 311. The electrical conductor 311 can include interconnects, including, but not limited to, SMP connectors and/or cables, U.FL connectors, mezzanine connectors, or the like. The conductor 311 provides a signal transmission path between the receive antenna 306b and the receive circuit 310 to direct a signal detected by the receive antenna 306b to the receive circuit 310 and a signal transmission path between the transmit circuit 308 and the transmit antenna 306a to direct a signal transmitted by the transmit antenna 306a. The conductor 311 can form a direct signal path between the respective antenna 306a, 306b and the respective circuit 308, 310, or intermediate electrical components (not illustrated) can be provided on the signal path between the respective antenna 306a, 306b and the respective circuit 308, 310.

The substrate 350 can include a number of different components including the controller that controls the operation of the sensor 300. The substrate 350 can take any of a large variety of forms, for example, in the form of a circuit board or printed circuit board (PCB) in a single layer or stacked layer configuration. For example, the substrate 350 can include a RF module or MF module 352 that can be a circuit to which the transmit circuit 308 and the receive circuit 310 are mounted on. In an embodiment, the RF module or MF module 352 can be mounted on and/or electrically connected to a System on a Chip (SoC) module 354 that includes the controller for the sensor 300. The SoC module 354 can include any of a microcontroller, for example, to handle radio data packetization or managing a protocol or controlling the function of the sensor, a microprocessor, memory, communication interfaces, timers, peripherals, power management circuits, AD or DA converters, etc. The SoC module 354 can be provided for integrating the components of the non-invasive analyte sensor system as a single integrated circuit, e.g., integrate the system function in a single module. In an embodiment, the SoC module 354 is mounted on a carrier PCB 356 and is electrically connected to Wi-Fi module 370 for transmitting data externally to a user device and/or a remote server or to the Internet for data processing and/or storage. It is appreciated that the Wi-Fi module 370 can also include other wireless connections such as Bluetooth, wireless data connections such a 4G, 5G, LTE or the like. The PCB 356 can be electrically connected to a power source 360, which can be a battery, external shore power source, a wake-up chip, or the like that can be provided internally of the housing 320 or external to the housing 320 and connected to the sensor 300, e.g., via USB connectors, such as, but not limited to USB-A, USB-B, USB-C, Micro-USB, or the like, barrel connectors, conductive charging contacts, or the like. The power source 360 provides the power to charge the battery and/or for powering the microcontroller, transmit and receive circuits, etc. for operation of the sensor 300.

With further reference to FIG. 3, the sensor 300 the sensor housing 320 defines an interior space. Components of the sensor 300 may be attached to and/or disposed within the housing 320. For example, the transmit antenna 306a and the receive antenna 306b can be attached to a support substrate 322 disposed within the housing 320 (e.g., internal thereto spaced apart from the housing) or can be attached directly to the housing 320. In some embodiments, the antennas 306a, 306b may be entirely or partially within the interior space 325 of the housing 320. In some embodiments, the antennas 306a, 306b may be attached to the housing 320 but at least partially or fully located outside the interior space. In some embodiments, the transmit circuit 308, the receive circuit 310, and the controller 309 are attached to the housing 320 and disposed entirely within the sensor housing 320.

The sensor(s) 100, 200, 300 can include one or more electromagnetic force ("EMF") shields, also referred to as an electromagnetic shield, around at least one component of the sensor(s), e.g., at least the receive and/or transmit components, to at least partially electromagnetically isolate the component from radio frequency electromagnetic waves and/or microwave frequency electromagnetic waves. The electromagnetic shield(s) described herein is outside, e.g., is not in the propagating pathway, of the signal transmission path between the receive antenna and the transmit antenna to the target. As such, the EMF shield can be used to separate different electrical components of the non-invasive analyte sensor system, e.g., the RF module, e.g., PCB having the transmit circuit, receive circuit, or antennas, or any of the other electrical components thereof, e.g., SoM/SoC, carrier PCB, etc., from other electrical components that may be on and near the signal transmission path, e.g., electromagnetically isolates the electrical component from sending and/or receiving radio frequency interference and/or microwave frequency interference signals. In an embodiment, the EMF shield can be provided at every power step to shield each of the electrical components separately at each power step. As referred to herein, electrical components are discrete devices in the analyte sensor that form an electronic circuit on which the electrical terminals or leads are provided, e.g., the circuitry, as opposed to individual components, e.g., the antenna alone.

For example, it was found that there can be seven major ways RF/MF interference, e.g., noise, could enter the sensor as a source or picked up by the element, as follows:

USB Input—can be source and/or pickup device for interference in the sensor. For example, power or the laptop connection connected to the sensor via USB and the USB cable itself can be the source or pickup area for RF/MF interfering signals.

SOM—can be a source for RF/MF interfering signals.

WiFI Antenna—can be a source and/or pickup device for RF/MF interfering signals.

SOM to RF generator interconnect—can be a pickup device for RF/MF interfering signals.

RF—can be a source of RF/MF interfering signals.

RF to Antenna interconnect—can be a pickup device for RF/MF interfering signals.

The environment—can be a source of RF/MF interfering signals.

As such, different housing configurations and/or electromagnetic shielding arrangements for the sensor are discussed herein to reduce the RF/MF interference for the sensor, for example, by reducing noise and/or EMF signals by 90%, 95%, 98%, or 99% for the EMF shielded component. It is understood that such disclosure is not intended to be limiting in scope, but rather, provides a discussion of specific embodiments with respect to the above RF/MF interference sources and signal pickup devices. It is understood that various arrangements of the EMF shielding can be provided to limit the RF/MF interfering signals.

Figure 4:
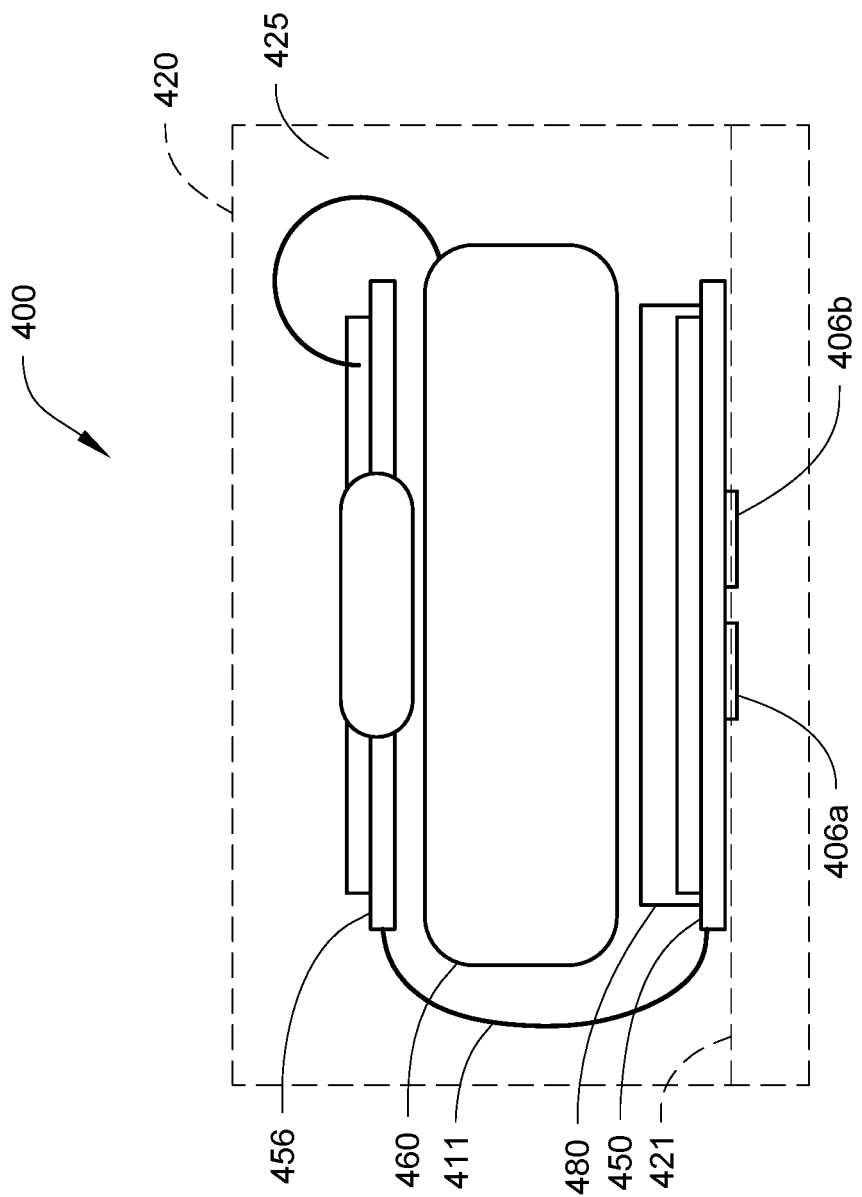
FIG. 4 is a schematic depiction of a non-invasive analyte sensor system with an electromagnetic shield according to an embodiment.

In an embodiment as illustrated in FIG. 4, a non-invasive analyte sensor system 400 having a EMF shield 480 is schematically shown. The sensor 400 is similar to the sensors discussed above and can include the same or similar elements which are referenced using the same reference numerals. In FIG. 4, the sensor 400 includes an antenna array that includes a plurality of transmit antennas 406a (which can include a single antenna or two or more antennas) and a plurality of receive antennas 406b (which can include a single antenna or two or more antennas) that are disposed on one surface of a substrate 450 which are enclosed by a housing 420. At least one battery 460, such as a rechargeable battery, is provided above the substrate 450, for providing power to the sensor device 400. In addition, a PCB 456 is provided on which the transmit circuit (e.g., 108, 208, 308), the receive circuit (e.g., 110, 210, 310), and the controller (e.g., 112, 209, 309) and other electronics of the sensory system can be disposed. The substrate 450 and the PCB 456 are electrically connected via any suitable electrical connection, such as a flexible connector 411, via wirings, flexible cables, interconnects or the like. An EMF shield 480 may be positioned between the antennas 406a, 406b and the battery 460, or between the antennas 406a, 406b and the PCB 456, to electromagnetically shield the circuitry and electrical components from RF and/or MF interference.

As depicted in FIG. 4, all of the elements of the sensor device 400, including the antennas 406a, 406b, the transmit circuit (e.g., 108, 208, 308), the receive circuit (e.g., 110, 210, 310), the controller (e.g., 112, 209, 309), the battery 460 and the like are contained entirely within the interior space 425 of the housing 420. In an alternative embodiment, a portion of or the entirety of each antenna 406a, 406b can project below a bottom wall 421 of the housing 420. In another embodiment, the bottom of each antenna 406a, 406b can be level with the bottom wall 421, or they can be slightly recessed from the bottom wall 421.

Figure 5:
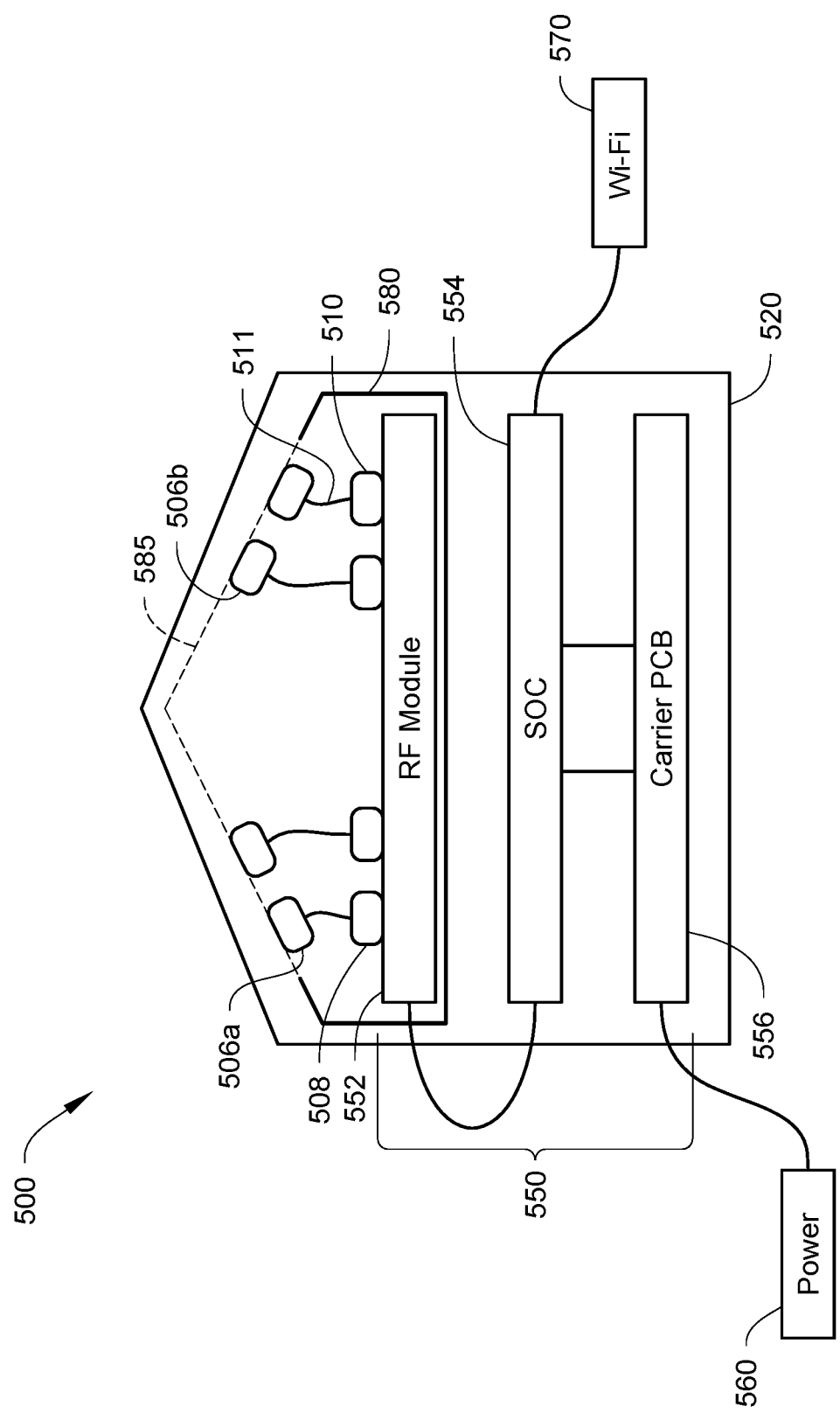
FIG. 5 is a schematic depiction of a non-invasive analyte sensor system with an electromagnetic shield according to another embodiment.

In another embodiment as illustrated in FIG. 5, a non-invasive analyte sensor system 500 having a EMF shield 580 is schematically shown. The sensor 500 is similar to the sensors discussed above and can include the same or similar elements which are referenced using the same reference numerals. In FIG. 5, the sensor 500 includes an antenna array that includes a plurality of transmit antennas 506*a* (which can include a single antenna or two or more antennas) and a plurality of receive antennas 506*b* (which can include a single antenna or two or more antennas) that are disposed on one surface of a substrate 550 which are enclosed by a housing 520. At least one power source 560, e.g., a rechargeable battery, is electrically connected to the substrate 550, for providing power to the sensor device 500. The sensor 500 further includes a transmit circuit 508, a receive circuit 510, and a controller, which can be mounted on the substrate 550.

The substrate 550 can include a number of different components including the controller that controls the operation of the sensor 500. The substrate 550 can take any of a large variety of forms, for example, in the form of a circuit board or printed circuit board (PCB). For example, the substrate 550 can include RF module or MF module 552 that can be a circuit to which the transmit circuit 508 and the receive circuit 510 are mounted and connected to the antennas via wiring 511. In an embodiment, the RF module or MF module 552 can be mounted on and/or electrically connected to a System on a Chip (SoC) module 554 that includes the controller for the sensor 500. In an embodiment, the SoC module 554 is mounted on a carrier PCB 556 and is electrically connected to Wi-Fi module 570 for transmitting data externally to a user device and/or a remote server or to the Internet for data processing and/or storage. The substrate 550 and any components therein can be electrically connected via any suitable electrical connections, such as flexible connectors, pins, interconnects, or the like.

As illustrated in FIG. 5, the EMF shield 580 is provided to at least partially electromagnetically isolate the RF module 552 including the plurality of transmit antennas 506*a* and plurality of receive antennas 506*b*. The EMF shield 580 also includes an opening that includes transmission part 585 that allows the transmission of the signal from the plurality of transmit antennas 506*a* and detection of the response signal by the plurality of receive antennas 506*b* of the sensor 500, e.g., in the propagating/signal transmission path of the antennas. The transmission part 585 can be the support substrate (e.g., 322) and can be made from a material that allows the transmission of the RF or MF electromagnetic wave with little to no interference in the signal, e.g., a top wall (or bottom wall) made of a polymer or plastic that allows RF or MF signal transmission. The transmission part 585 can be spaced 0.25 to 1 mm from the outer housing 520, e.g., the housing 520 can have a thickness between 0.25 to 1 mm and/or filled with resin. Since the remainder of the EMF shield 580 is made (or completely formed) of a material that prevents or substantially limits transmission of signals in the RF band and/or MF band, e.g., by having a reduction of 90%, 95%, 98%, 99% in noise and/or EMF signals, not only is the RF module 552 (and components thereon) isolated from extraneous RF and/or MF signals from external sources which can cause RF and/or MF interference when processing the signals by the antennas and result in inaccurate measurements and/or interfere with the signals for operation of the sensor 500, the EMF shield 580 prevents or substantially limits transmission of the RF and/or MF signal in a direction other than the propagating direction, e.g., by having a reduction of 90%, 95%, 98%, 99% in noise and/or EMF signals. As such, the sensor 500 has limited output of the RF and MF signals that may degrade the performance of external equipment and is compliant for use in a hospital setting, e.g., does not interfere or limits interference with other medical equipment, such as, pacemakers, patient vital monitors, neonatal heaters, etc. Moreover, since at least the receive antennas 506*b* of the sensor 500 are electromagnetically isolated, e.g., by having a reduction of 90%, 95%, 98%, 99% in noise and/or EMF signals and/or any reflections thereof, a greater accuracy of the sensing of the analyte can be obtained, since any noise and/or stray EMF signals are not received by the receive antennas 506*b*.

Figure 6:
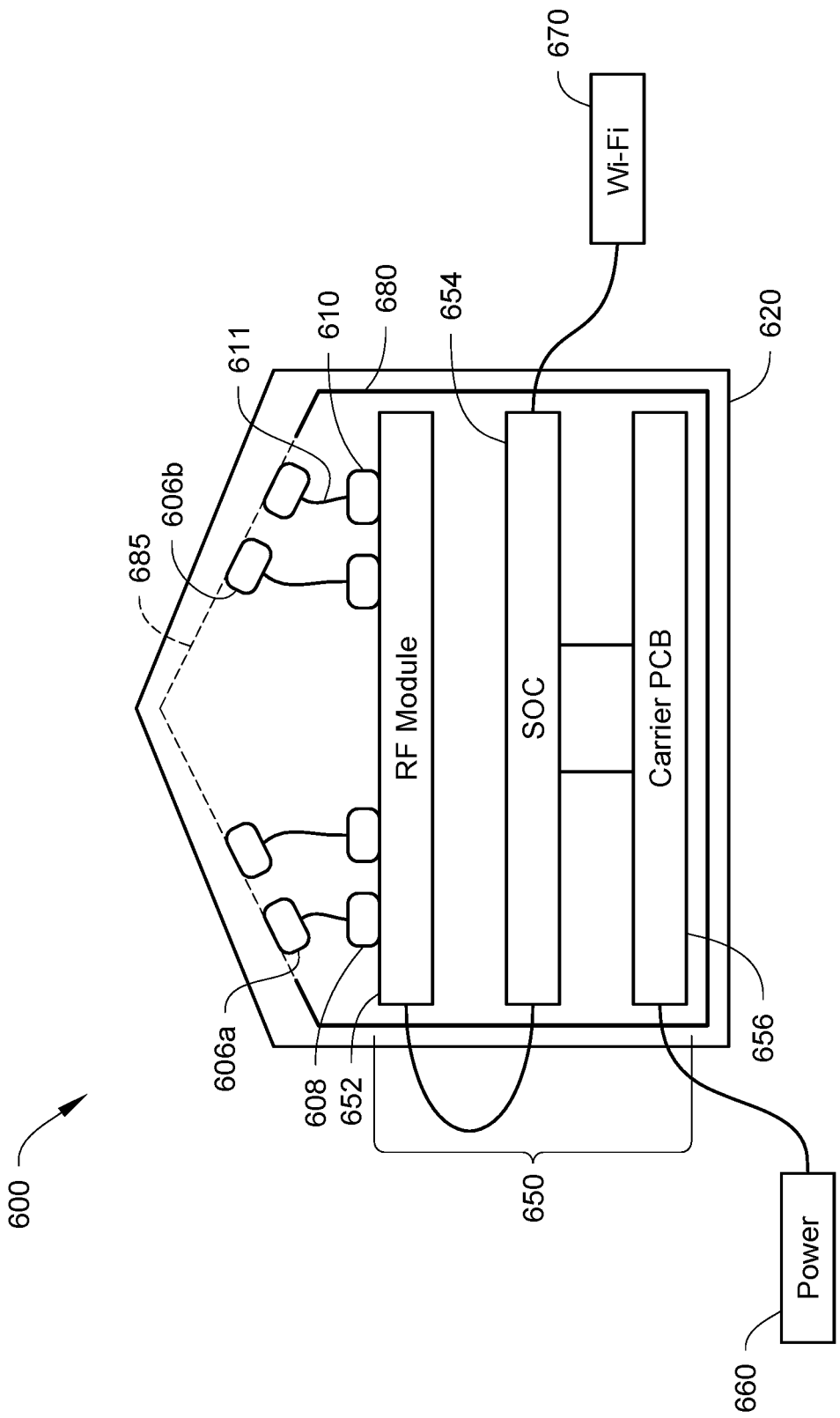
FIG. 6 is a schematic depiction of a non-invasive analyte sensor system with an electromagnetic shield according to another embodiment.

In another embodiment as illustrated in FIG. 6, a non-invasive analyte sensor system 600 having a EMF shield 680 is schematically shown. The sensor 600 is similar to the sensors discussed above and can include the same or similar elements which are referenced using the same reference numerals. In FIG. 6, the sensor 600 includes an antenna array that includes a plurality of transmit antennas 606*a* (which can include a single antenna or two or more antennas) and a plurality of receive antennas 606*b* (which can include a single antenna or two or more antennas) that are disposed on one surface of a substrate 650 which are enclosed by a housing 620. At least one power source 660, e.g., a rechargeable battery, is electrically connected to the substrate 650, for providing power to the sensor device 600. The sensor 600 further includes a transmit circuit 608, a receive circuit 610, and a controller, which can be mounted on the substrate 650.

The substrate 650 can include a number of different components including the controller that controls the operation of the sensor 600. The substrate 650 can take any of a large variety of forms, for example, in the form of a circuit board or printed circuit board (PCB). For example, the substrate 650 can include RF module or MF module 652 that can be a circuit to which the transmit circuit 608 and the receive circuit 610 are mounted and connected to the antennas via wiring 611. In an embodiment, the RF module or MF module 652 can be mounted on and/or electrically connected to a System on a Chip (SoC) module 654 that includes the controller for the sensor 600. In an embodiment, the SoC module 654 is mounted on a carrier PCB 656 and is electrically connected to Wi-Fi module 670 for transmitting data externally to a user device and/or a remote server or to the Internet for data processing and/or storage. The substrate 650 and any components therein can be electrically connected via any suitable electrical connections, such as flexible connectors, pins, interconnectors, or the like.

As illustrated in FIG. 6, the EMF shield 680 is provided to at least partially electromagnetically isolate the entire substrate 650 including the plurality of transmit antennas 606*a* and plurality of receive antennas 606*b*. The EMF shield 680 also includes an opening that include transmission part 685 that allows the transmission of the signal from the plurality of transmit antennas 606*a* and detection of the response signal by the plurality of receive antennas 606*b* of the sensor 600, e.g., in the propagating/signal transmission path of the antennas. The transmission part 685 can be the support substrate (e.g., 322) and can be made from a material that allows the transmission of the RF or MF electromagnetic wave with little to no interference in the signal, e.g., a top wall (or bottom wall) made of a polymer or plastic that allows RF or MF signal transmission. The transmission part 685 can be spaced 0.25 to 1 mm from the outer housing 620, e.g., the housing 620 can have a thickness between 0.25 to 1 mm and/or filled with resin. Since the remainder of the EMF shield 680 is made (or completely formed) of a material that prevents or substantially limits transmission of signals in the RF band and/or MF band, e.g., by having a reduction of 90%, 95%, 98%, 99% in noise and/or EMF signals, not only is the RF module 652 (and components thereon) isolated from extraneous RF and/or MF signals from external sources which can cause RF and/or MF interference when processing the signals and result in inaccurate measurements and/or interfere with the signals for operation of the sensor 600, the EMF shield 680 prevents or substantially limits transmission of any RF and/or MF signals from any of the components in a direction other than the propagating direction e.g., by having a reduction of 90%, 95%, 98%, 99% in noise and/or EMF signals and/or reflections thereof. As such, the sensor 600 has limited output of the RF and MF signals that may degrade the performance of external equipment and is compliant for use in a hospital setting, e.g., does not interfere or limits interference with other medical equipment, such as, pacemakers, patient vital monitors, neonatal heaters, etc. and reduces the noise and/or EMF signals received by the receive antennas 606b.

Figure 7:
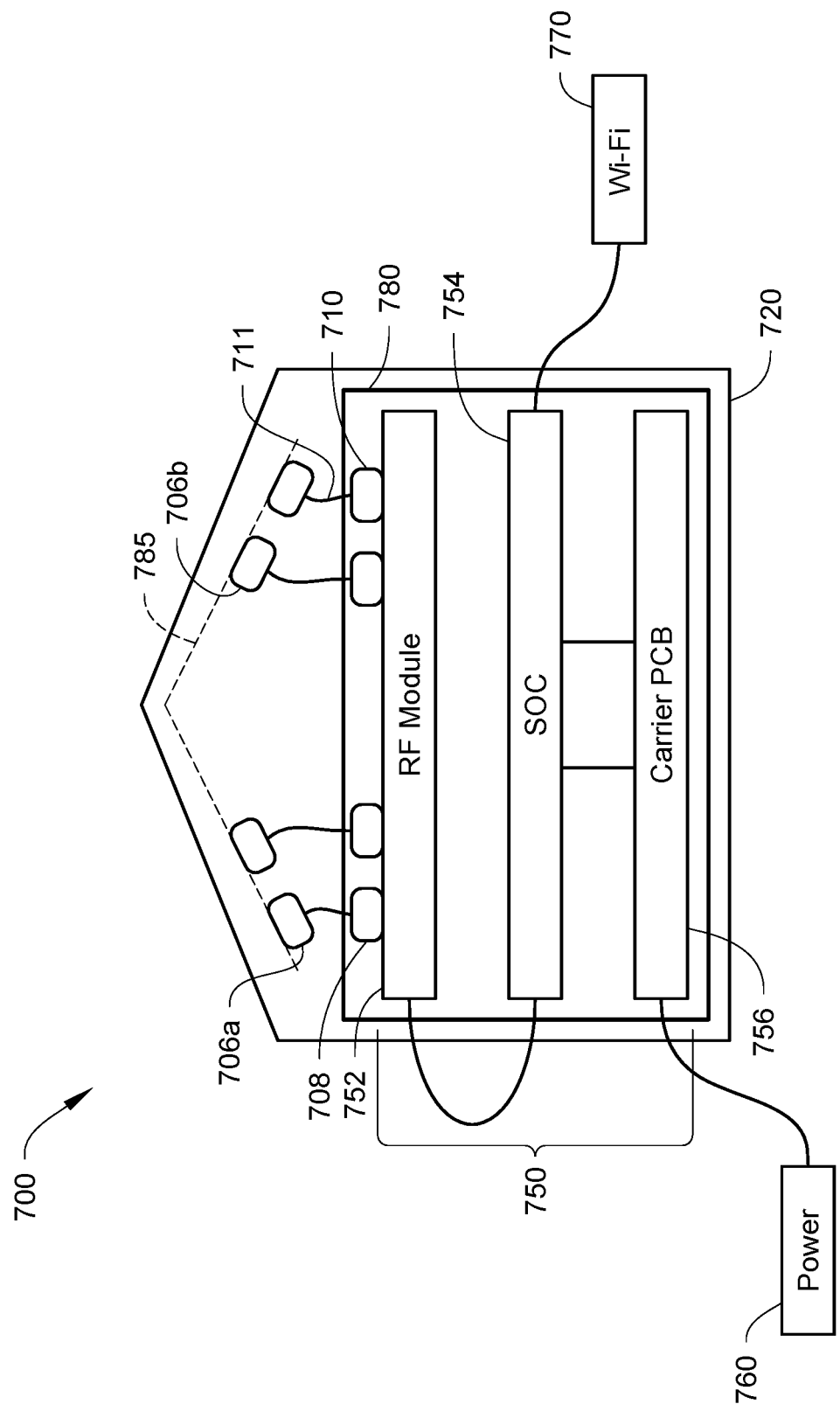
FIG. 7 is a schematic depiction of a non-invasive analyte sensor system with an electromagnetic shield according to yet another embodiment.

In another embodiment as illustrated in FIG. 7, a non-invasive analyte sensor system 700 having a EMF shield 780 is schematically shown. The sensor 700 is similar to the sensors discussed above and can include the same or similar elements which are referenced using the same reference numerals. In FIG. 7, the sensor 700 includes an antenna array that includes a plurality of transmit antennas 706a (which can include a single antenna or two or more antennas) and a plurality of receive antennas 706b (which can include a single antenna or two or more antennas) that are disposed on one surface of a substrate 750 which are enclosed by a housing 720. At least one power source 760, e.g., a rechargeable battery, is electrically connected to the substrate 750, for providing power to the sensor device 700. The sensor 700 further includes a transmit circuit 708, a receive circuit 710, and a controller, which can be mounted on the substrate 750.

The substrate 750 can include a number of different components including the controller that controls the operation of the sensor 700. The substrate 750 can take any of a large variety of forms, for example, in the form of a circuit board or printed circuit board (PCB). For example, the substrate 750 can include RF module or MF module 752 that can be a circuit to which the transmit circuit 708 and the receive circuit 710 are mounted and connected to the antennas via wiring 711. In an embodiment, the RF module or MF module 752 can be mounted on and/or electrically connected to a System on a Chip (SoC) module 754 that includes the controller for the sensor 700. In an embodiment, the SoC module 754 is mounted on a carrier PCB 756 and is electrically connected to Wi-Fi module 770 for transmitting data externally to a user device and/or a remote server or to the Internet for data processing and/or storage. The substrate 750 and any components therein can be electrically connected via any suitable electrical connections, such as flexible connectors, pins, interconnects, or the like.

As illustrated in FIG. 7, the EMF shield 780 is provided to at least partially electromagnetically isolate the substrate 750 in which the plurality of transmit antennas 706a and plurality of receive antennas 706b are not electromagnetically isolated. The plurality of transmit antennas 706a and the plurality of receive antennas 706b can be supported by a transmission part 785, which can be the support substrate (e.g., 322). The transmission part 785 can be spaced 0.25 to 1 mm from the outer housing 720, e.g., the housing 720 can have a thickness between 0.25 to 1 mm and/or filled with resin Since the plurality of transmit antennas 706a and the plurality of receive antennas 706b can have any arrangement and orientation relative to the target that is sufficient to allow transmission and detection of the response signal(s) to allow the analyte sensing to take place, e.g., in the propagating direction, a substantial amount of RF interference or MF interference does not occur due to the transmission and receipt of the sensing/response signals. The EMF shield 780 is made (or completely formed) of a material that prevents or substantially limits transmission in the RF band and/or MF band, e.g., by having a reduction of 90%, 95%, 98%, 99% in noise and/or EMF signals, such that not only is the substrate 750 (and components thereon) isolated from extraneous RF and/or MF signals from external sources or reflections therein, which can cause RF and/or MF interference when processing the signals by the antennas and result in inaccurate measurements, the EMF shield 780 prevents or substantially limits transmission of the RF and/or MF signal to external devices or the environment. As such, the sensor 700 has limited output of the RF and MF signals that may degrade the performance of external equipment and is compliant for use in a hospital setting, e.g., does not interfere or limits interference with other medical equipment, such as, pacemakers, patient vital monitors, neonatal heaters, etc.

In another embodiment as illustrated in FIG. 8, a non-invasive analyte sensor system 800 having a EMF shield 880 is schematically shown. The sensor 800 is similar to the sensors discussed above and can include the same or similar elements which are referenced using the same reference numerals. In FIG. 8, the sensor 800 includes an antenna array that includes a plurality of transmit antennas 806a (which can include a single antenna or two or more antennas) and a plurality of receive antennas 806b (which can include a single antenna or two or more antennas) that are disposed on one surface of a substrate 850 which are enclosed by a housing 820. At least one power source 860, e.g., a rechargeable battery, is electrically connected to the substrate 850, for providing power to the sensor device 800. The sensor 800 further includes a transmit circuit 808, a receive circuit 810, and a controller, which can be mounted on the substrate 850.

The substrate 850 can include a number of different components including the controller that controls the operation of the sensor 800. The substrate 850 can take any of a large variety of forms, for example, in the form of a circuit board or printed circuit board (PCB). For example, the substrate 850 can include RF module or MF module 852 that can be a circuit to which the transmit circuit 808 and the receive circuit 810 are mounted and connected to the antennas via wiring 811. In an embodiment, the RF module or MF module 852 can be mounted on and/or electrically connected to a System on a Chip (SoC) module 854 that includes the controller for the sensor 800. In an embodiment, the SoC module 854 is mounted on a carrier PCB 856 and is electrically connected to Wi-Fi module 870 for transmitting data externally to a user device and/or a remote server or to the Internet for data processing and/or storage. The substrate 850 and any components therein can be electrically connected via any suitable electrical connections, such as flexible connectors, pins, interconnects, or the like.

As illustrated in FIG. 8, the EMF shield 880 is provided to at least partially electromagnetically isolate the SoC module 854 and the PCB 856 but does not electromagnetically isolate the RF module 852 and the plurality of transmit antennas 806a and plurality of receive antennas 806b. The plurality of transmit antennas 806a and the plurality of receive antennas 806b can be supported by a transmission part 885, which can be the support substrate (e.g., 322). The transmission part 885 can be spaced 0.25 to 1 mm from the outer housing 820, e.g., the housing 820 can have a thickness between 0.25 to 1 mm and/or filled with resin. Since the plurality of transmit antennas 806a and the plurality of receive antennas 806b can have any arrangement and orientation relative to the target that is sufficient to allow transmission and detection of the response signal(s) to allow the analyte sensing to take place, e.g., in the propagating direction, a substantial amount of RF interference or MF interference does not occur due to the transmission and receipt of the sensing/response signals. The EMF shield 880 is made (or completely formed) of a material that prevents or substantially limits transmission in the RF band and/or MF band, e.g., by having a reduction of 90%, 95%, 98%, 99% in noise and/or EMF signals, not only are the SoC module 854 and the PCB 856 (and components thereon) isolated from extraneous RF and/or MF signals from external sources and from the RF module 852 and the antennas 806a, 806b, which can interfere with the control signals of the SoC module 854, the EMF shield 880 prevents or substantially limits transmission of the RF and/or MF signal to external devices or the environment, e.g., by having a reduction of 90%, 95%, 98%, 99% in noise and/or EMF signals. As such, the sensor 800 has limited output of the RF and MF signals that may degrade the performance of external equipment and is compliant for use in a hospital setting, e.g., does not interfere or limits interference with other medical equipment, such as, pacemakers, patient vital monitors, neonatal heaters, etc.

In another embodiment as illustrated in FIG. 9, a non-invasive analyte sensor system 900 having a EMF shield 980 is schematically shown. The sensor 900 is similar to the sensors discussed above and can include the same or similar elements which are referenced using the same reference numerals. In FIG. 9, the sensor 900 includes an antenna array that includes a plurality of transmit antennas 906a (which can include a single antenna or two or more antennas) and a plurality of receive antennas 906b (which can include a single antenna or two or more antennas) that are disposed on one surface of a substrate 950 which are enclosed by a housing 920. At least one power source 960, e.g., a rechargeable battery, is electrically connected to the substrate 950, for providing power to the sensor device 900. The sensor 900 further includes a transmit circuit 908, a receive circuit 910, and a controller, which can be mounted on the substrate 950.

The substrate 950 can include a number of different components including the controller that controls the operation of the sensor 900. The substrate 950 can take any of a large variety of forms, for example, in the form of a circuit board or printed circuit board (PCB). For example, the substrate 950 can include RF module or MF module 952 that can be a circuit to which the transmit circuit 908 and the receive circuit 910 are mounted and connected to the antennas via wiring 911. In an embodiment, the RF module or MF module 952 can be mounted on and/or electrically connected to a System on a Chip (SoC) module 954 that includes the controller for the sensor 900. In an embodiment, the SoC module 954 is mounted on a carrier PCB 956 and is electrically connected to Wi-Fi module 970 for transmitting data externally to a user device and/or a remote server or to the Internet for data processing and/or storage. The substrate 950 and any components therein can be electrically connected via any suitable electrical connections, such as flexible connectors, pins, interconnects, or the like.

As illustrated in FIG. 9, two EMF shields 980, 982 are provided. A first EMF shield 980 is provided to at least partially electromagnetically isolate the RF module 952, which includes the transmit circuit 908 and receive circuit 910 and corresponding plurality of transmit antennas 906a and plurality of receive antennas 906b. The EMF shield 980 also includes an opening that includes transmission part 985 that allows the transmission of the signal from the plurality of transmit antennas 906a and detection of the response signal by the plurality of receive antennas 906b of the sensor 900, e.g., in the propagating/signal transmission path of the antennas. The transmission part 985 can be the support substrate (e.g., 322) and can be made from a material that allows the transmission of the RF or MF electromagnetic wave with little to no interference in the signal. A second EMF shield 982 at least partially electromagnetically isolates the SoC module 954 and the PCB 956. The transmission part 985 can be spaced 0.25 to 1 mm from the outer housing 920, e.g., the housing 920 can have a thickness between 0.25 to 1 mm and/or filled with resin. As such, since the remainder of the EMF shield 980 is made (or completely formed) of a material that prevents or substantially limits transmission in the RF band and/or MF band, the RF module 952 (and components thereon) is isolated from extraneous RF and/or MF signals from external sources which can cause RF and/or MF interference when processing the signals by the antennas and result in inaccurate measurements, and prevents or substantially limits transmission of the RF or MF signal in a direction other than the propagating direction e.g., by having a reduction of 90%, 95%, 98%, 99% in noise and/or EMF signals. Additionally, since the second EMF shield 982 is made (or completely formed) of a material that prevents or substantially limits transmission in the RF band and/or MF band, e.g., by having a reduction of 90%, 95%, 98%, 99% in noise and/or EMF signals, the SoC module 954 and the PCB 956 (and components thereon) are isolated from extraneous RF and/or MF signals from external sources and from the RF module 952 and the antennas, which can interfere with the control signals of the SoC module 954, and prevents or substantially limits transmission of the RF and/or MF signal to external devices or the environment. As such, the sensor 900 has limited output of the RF and MF signals that may degrade the performance of external equipment and is compliant for use in a hospital setting, e.g., does not interfere or limits interference with other medical equipment, such as, pacemakers, patient vital monitors, neonatal heaters, etc. Moreover, since at least the receive antennas 906b of the sensor 900 are electromagnetically isolated, e.g., by having a reduction of 90%, 95%, 98%, 99% in noise and/or EMF signals and/or reflections therein, a greater accuracy of the sensing of the analyte can be obtained, since the noise and/or stray EMF signals are reduced and not received by the receive antennas 906b.

Figure 10A:
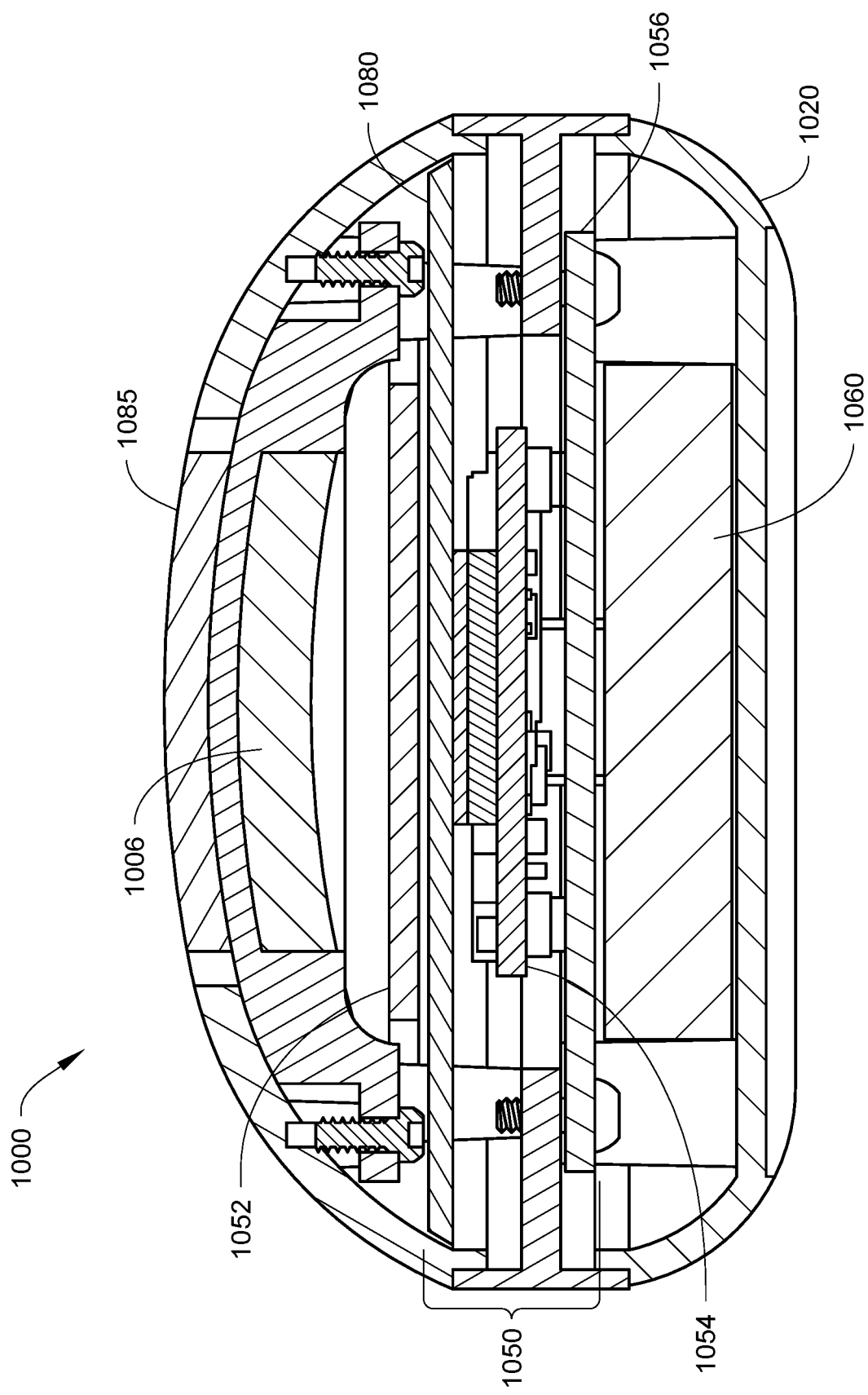
FIG. 10A is an illustration of a non-invasive analyte sensor system with an electromagnetic shield according to still another embodiment.
Figure 10B:
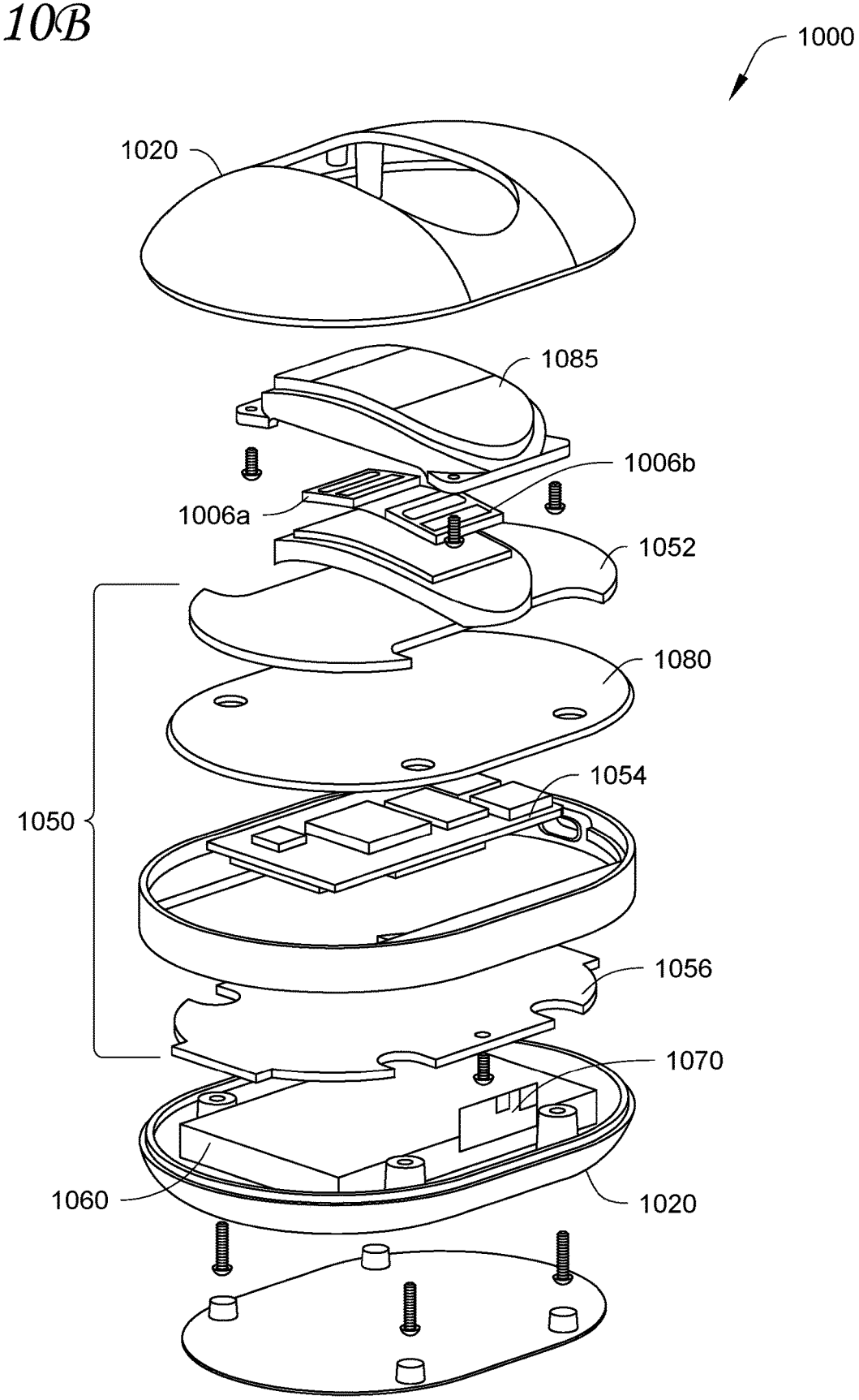
FIG. 10B is an exploded view of the non-invasive analyte sensor system according to FIG. 10A.

In yet another embodiment as illustrated in FIGS. 10A and 10B, a non-invasive analyte sensor system 1000 having a EMF shield 1080 is provided. The sensor 1000 is similar to the sensors discussed above and can include the same or similar elements which are referenced using the same reference numerals. In FIGS. 10A and 10B, the sensor 1000 includes an antenna array 1006 that includes a plurality of transmit antennas 1006a (which can include a single antenna or two or more antennas) and a plurality of receive antennas 1006b (which can include a single antenna or two or more antennas) that are disposed on one surface of a substrate 1050 which are enclosed by a housing 1020. At least one power source 1060, e.g., a rechargeable battery, is electrically connected to the substrate 1050, for providing power to the sensor device 1000. The sensor 1000 further includes a transmit circuit (not shown), a receive circuit (not shown), and a controller, which can be mounted on the substrate 1050.

The substrate 1050 can include a number of different components including the controller that controls the operation of the sensor 1000. The substrate 1050 can take any of a large variety of forms, for example, in the form of a circuit board or printed circuit board (PCB). For example, the substrate 1050 can include RF module or MF module 1052 that can be a circuit to which the transmit circuit and the receive circuit are mounted. In an embodiment, the RF module or MF module 1052 can be mounted on and/or electrically connected to a System on a Chip (SoC) module 1054 that includes the controller for the sensor 1000. In an embodiment, the SoC module 1054 is mounted on a carrier PCB 1056 and is electrically connected to Wi-Fi module 1070 for transmitting data externally to a user device and/or a remote server or to the Internet for data processing and/or storage. The substrate 1050 and any components therein can be electrically connected via any suitable electrical connections, such as flexible connectors, pins, interconnects, or the like.

As illustrated in FIGS. 10A and 10B, the EMF shield 1080 can be provided within the housing 1020 to electromagnetically isolate and separate the RF module or MF module 1052 (and transmit and receive circuits) from the SoC module 1054, the carrier PCB 1056, and the power source 1060. The housing 1020 can include an opening that includes transmission part 1085, e.g., a sensor cover, that allows the transmission of the signal from the plurality of transmit antennas 1006a and detection of the response signal by the plurality of receive antennas 1006b of the sensor 1000, e.g., in the propagating/signal transmission path of the antennas. The transmission part 1085 can be the support substrate (e.g., 322) and can be made from a material that allows the transmission of the RF or MF electromagnetic wave with little to no interference in the signal, for example, a part of the housing that does not include the carbon nanotubes or material that has high electrical conductivity and high dielectric constant. The transmission part 1085 can have a thickness between 0.25 to 1 mm and/or the opening can be filled with resin to cover the plurality of transmit antennas and the plurality of receive antennas. Since the housing 1020 is separated by the EMF shield 1080 that is made (or completely formed) of a material that prevents or substantially limits transmission in the RF band or MF band, e.g., by having a reduction of 90%, 95%, 98%, 99% in noise and/or EMF signals, the plurality of transmit antennas 1006a and the plurality of receive antennas 1006b and corresponding circuitry are electromagnetically isolated from extraneous RF and/or MF signals from external sources and from the remaining electrical components of the sensor 1000 and reflections therein, which can cause RF and/or MF interference when processing the signals by the antennas and result in inaccurate measurements. In an embodiment, the EMF shield 1080 can be spaced between 2 to 6 mm or about 5 mm from the carrier PCB. The EMF shield 1080 can also include RF gasketing between the EMF shield 1080 and any metal parts. For example, in an embodiment, the EMF shield 1080 can be a metal sheet or foil, a wire metal mesh, metal or polymer coated film, or PCB with a metal layer and/or a material that can be electrically activated and/or include electrically conductive carbon nanotubes or other material that has high electrical conductivity and a high dielectric constant.

While FIGS. 10A and 10B illustrate the EMF shield 1080 as being a sheet or foil, such disclosure is not intended to be limiting in scope. Rather, such disclosure is provided to illustrate that various components can be electromagnetically isolated to provide electromagnetic shielding/isolation as needed. For example, in an embodiment, each of the various components of the sensor 1000 can be electromagnetically isolated, e.g., at each power step, including any of the conductors, wires, connectors, interconnects, or the like connecting the same using an electromagnetically shielding coating or spray. Similarly, in any of the embodiments, RF gasketing can be provided between the EMF shield and corresponding components to provide further shielding/isolation or between any connection or interconnect.

In yet another embodiment as illustrated in FIG. 11, a non-invasive analyte sensor system 1100 having a EMF shield 1180 is provided. The sensor 1100 is similar to the sensors discussed above and can include the same or similar elements which are referenced using the same reference numerals. In FIG. 11, the sensor 1100 includes an antenna array 1106 that includes a plurality of transmit antennas (which can include a single antenna or two or more antennas) and a plurality of receive antennas (which can include a single antenna or two or more antennas) that are disposed on one surface of a substrate 1150 which are enclosed by a housing 1120. At least one power source 1160, e.g., a rechargeable battery, is electrically connected to the substrate 1150, for providing power to the sensor device 1100. The sensor 1100 further includes a transmit circuit (not shown), a receive circuit (not shown), and a controller, which can be mounted on the substrate 1150.

The substrate 1150 can include a number of different components including the controller that controls the operation of the sensor 1100. The substrate 1150 can take any of a large variety of forms, for example, in the form of a circuit board or printed circuit board (PCB). For example, the substrate 1150 can include RF module or MF module 1152 that can be a circuit to which the transmit circuit and the receive circuit are mounted. In an embodiment, the RF module or MF module 1152 can be mounted on and/or electrically connected to a System on a Chip (SoC) module 1154 that includes the controller for the sensor 1100. In an embodiment, the SoC module 1154 is mounted on a carrier PCB 1156 and is electrically connected to Wi-Fi module for transmitting data externally to a user device and/or a remote server or to the Internet for data processing and/or storage. The substrate 1150 and any components therein can be electrically connected via any suitable electrical connections, such as flexible connectors, pins, etc.

As illustrated in FIG. 11, the EMF shield 1180 can be provided within the housing 1120 to electromagnetically isolate and separate the SoC module 1154 from the RF or MF module 1152 and associated antennas. The EMF shield 1180 can have a thickness of at least 0.3 mm, and preferably between 0.3 and 0.6 mm. The housing 1120 can include an opening that includes transmission part 1185, e.g., a sensor cover, that allows the transmission of the signal from the plurality of transmit antennas and detection of the response signal by the plurality of receive antennas of the sensor 1100, e.g., in the propagating/signal transmission path of the antennas. The transmission part 1185 can be the support substrate (e.g., 322) and can be made from a material that allows the transmission of the RF or MF electromagnetic wave with little to no interference in the signal, for example, a part of the housing that does not include the carbon nanotubes or material that has high electrical conductivity and high dielectric constant. In an embodiment, all of the connections for the plurality of transmit antennas and the plurality of receive antennas to the RF or MF module 1152 are in the center directly above the shielded area. The transmission part 1185 can have a thickness between 0.25 to 1 mm and/or the opening can be filled with resin to cover the plurality of transmit antennas and the plurality of receive antennas. Since the SoC module 1154 is separated by the EMF shield 1180 that is made (or completely formed) of a material that prevents or substantially limits transmission in the RF band or MF band, e.g., by having a reduction of 90%, 95%, 98%, 99% in noise and/or EMF signals, the plurality of transmit antennas 1006*a* and the plurality of receive antennas 1006*b* and corresponding circuitry are electromagnetically isolated from extraneous and/or reflected RF and/or MF signals, which can cause RF and/or MF interference when processing the signals by the antennas and result in inaccurate measurements. The EMF shield 1180 can also include RF gasketing between the EMF shield 1180 and any metal parts and/or connector shields around any thru-holes through the EMF shield 1180. For example, in an embodiment, any connections, e.g., connectors, between the various layers can include RF gasketing around the connection or raised walls, e.g., with RF or MF connector shields, surrounding the connections for further RF sealing/shielding.

While in the above embodiments, the EMF shield has been discussed to reduce the noise and/or EMF signals, it is appreciated that when the non-invasive analyte sensor system is attached or coupled to an arm of a patient, the arm of the patient can also be part of the EMF shielding system. For example, since the antennas are close or adjacent to the arm of the patient, the arm of the patient can reduce the amount of noise and/or EMF signals received by the receive antenna to further electromagnetically isolate the sensor from stray or interfering signals from external device.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A non-invasive analyte sensor system, comprising:
a housing comprising a first wall, a second wall, and an internal space therebetween;
a printed circuit board within the internal space;
a first antenna array arranged between a first side of the printed circuit board and the second wall of the housing, the first antenna array comprising two or more antennas that are positioned and arranged to transmit a radio frequency transmit signal or a microwave frequency transmit signal into a target containing at least one analyte, at least a portion of the first antenna array projecting below the second wall of the housing;
a second antenna array arranged between the first side of the printed circuit board and the second wall of the housing, the second antenna array comprising two or more antennas that are positioned and arranged to detect a radio frequency response or a microwave frequency response resulting from transmission of the radio frequency transmit signal or the microwave frequency transmit signal by the first antenna array into the target containing the at least one analyte, at least a portion of the second antenna array projecting below the second wall of the housing;
a power source arranged between a second side of the printed circuit board and the first wall of the housing, the power source comprising a battery;
a transmit circuit that is electrically connectable to the first antenna array, the transmit circuit is configured to generate the radio frequency transmit signal or the microwave frequency transmit signal to be transmitted by the first antenna array;
a receive circuit that is electrically connectable to the second antenna array, the receive circuit is configured to receive the radio frequency response or the microwave frequency response detected by the second antenna array; and
at least one electromagnetic shield arranged between the first side of the printed circuit board and both the first antenna array and the second antenna array, wherein the at least one electromagnetic shield separates the internal space of the housing into a first portion and a second portion, wherein the at least one electromagnetic shield electromagnetically isolates the first antenna array, the second antenna array, the transmit circuit, and the receive circuit in the first portion from radio frequency interference and/or microwave frequency interference from other internal components of the non-invasive analyte sensor system in the second portion of the internal space of the housing.

2. The non-invasive analyte sensor system of claim 1, wherein the other internal components comprise a system on chip module, and further comprising at least a second electromagnetic shield that at least partially electromagnetically isolates the system on chip module and the printed circuit board.

3. The non-invasive analyte sensor system of claim 1, wherein the at least one analyte comprises glucose, blood ketones, carbon dioxide, melatonin, acetaminophen, oxygen, alcohol, calcium, vitamin C, a hydration indicator, white blood cells, luteinizing hormone, or prostaglandins, hormones including estrogen, progesterone, and/or follicle stimulating hormone (FSH).

4. The non-invasive analyte sensor system of claim 1, further comprising one or more radio frequency gaskets provided between the at least one electromagnetic shield and any metal parts.

5. The non-invasive analyte sensor system of claim 1, wherein the at least one electromagnetic shield includes a chamber having a height to separate the first antenna array, the second antenna array, the transmit circuit, and the receive circuit in the first portion from a system on chip module in the second portion.

6. The non-invasive analyte sensor system of claim 1, further comprising a system on chip module that includes a controller for controlling the non-invasive analyte sensor system, the printed circuit board, and the power source.

7. The non-invasive analyte sensor of claim 1, wherein the two or more antennas of the first antenna array comprises an antenna having a rectangular shape and an antenna having a rounded rectangle shape.

8. The non-invasive analyte sensor of claim 1, wherein the two or more antennas of the second antenna array comprises an antenna having a rounded rectangle shape and an antenna having a stadium shape.

9. The non-invasive analyte sensor of claim 1, wherein the two or more antennas of the first antenna array comprises a first antenna and a second antenna separated by a first space, and wherein the two or more antennas of the second antenna array comprises a third antenna and a fourth antenna separated by a second space, wherein the first antenna array and the second antenna array are separated by a third space, wherein the third space is greater than the first space and is greater than the second space.

10. The non-invasive analyte sensor of claim 1, wherein the first antenna array and the second antenna array are arranged on the same plane.

11. A non-invasive analyte sensor system, comprising:
a housing comprising a first wall, a second wall, and an internal space therebetween;
a printed circuit board within the internal space;
an antenna array arranged between a first side of the printed circuit board and the second wall of the housing, the antenna array having at least four antennas each of which is configured to emit and receive radio frequency electromagnetic waves or microwave frequency electromagnetic waves, at least a portion of the antenna array projecting below the second wall of the housing;
a power source arranged between a second side of the printed circuit board and the first wall of the housing, the power source comprising a battery;
a transmit circuit that is selectively electrically connectable to any one or more of the at least four antennas, the transmit circuit is configured to generate at least one transmit signal in a radio frequency range of the electromagnetic spectrum or a microwave frequency range of the electromagnetic spectrum to be transmitted into a target by the one or more of the at least four antennas the transmit circuit is electrically connected to;
a receive circuit that is selectively electrically connectable to any one or more of the at least four antennas, the receive circuit is configured to receive a response detected by the one or more of the at least four antennas the receive circuit is electrically connected to resulting from transmission of the at least one transmit signal into the target containing at least one analyte of interest;
electrical conductors electrically connecting the transmit circuit and the receive circuit with the at least four antennas; and
at least one electromagnetic shield arranged between the first side of the printed circuit board and the antenna array, wherein the at least one electromagnetic shield separates the internal space of the housing into a first portion and a second portion, wherein the at least one electromagnetic shield electromagnetically isolates the antenna array, the transmit circuit, and the receive circuit in the first portion from radio frequency interference and/or microwave frequency interference from other internal components of the non-invasive analyte sensor system in the second portion of the internal space of the housing.

12. The non-invasive analyte sensor system of claim 11, wherein the at least one analyte comprises glucose, blood ketones, carbon dioxide, melatonin, acetaminophen, oxygen, alcohol, calcium, vitamin C, a hydration indicator, white blood cells, luteinizing hormone, prostaglandins, and/or follicle stimulating hormone.

13. The non-invasive analyte sensor system of claim 11, wherein the other internal components comprise a system on chip module, and further comprising at least a second electromagnetic shield that at least partially electromagnetically isolates the system on chip module and the printed circuit board.

14. The non-invasive analyte sensor system of claim 11, further comprising a system on chip module that includes a controller for controlling the non-invasive analyte sensor system, the printed circuit board, and the power source.

15. The non-invasive analyte sensor of claim 11, wherein the at least four antennas of the antenna array comprises an antenna having a rectangular shape, an antenna having a rounded rectangle shape, and an antenna having a stadium shape.

16. The non-invasive analyte sensor of claim 11, wherein the at least four antennas of the antenna array comprises a first antenna and a second antenna separated by a first space, and a third antenna and a fourth antenna separated by a second space, wherein the first antenna and the second antenna are separated from the third antenna and the fourth antenna by a third space, wherein the third space is greater than the first space and is greater than the second space.

17. The non-invasive analyte sensor of claim 11, wherein each of the at least four antennas of the antenna array are arranged on the same plane.

18. A non-invasive analyte sensor system, comprising:
a housing comprising a first wall, a second wall, and an internal space therebetween;
a printed circuit board within the internal space;
a first antenna array arranged between a first side of the printed circuit board and the second wall of the housing, the first antenna array comprising two or more antennas that are positioned and arranged to transmit a radio frequency transmit signal or a microwave frequency transmit signal into a target containing at least one analyte, at least a portion of the first antenna array projecting below the second wall of the housing;
a second antenna array arranged on the first side of the printed circuit board, the second antenna array comprising two or more antennas that are positioned and arranged to detect a radio frequency response or a microwave frequency response resulting from transmission of the radio frequency transmit signal or the microwave frequency transmit signal by the first antenna array into the target containing the at least one analyte, at least a portion of the second antenna array projecting below the second wall of the housing;
a transmit circuit that is electrically connectable to the first antenna array, the transmit circuit is configured to generate the radio frequency transmit signal or the microwave frequency transmit signal to be transmitted by the first antenna array;
a receive circuit that is electrically connectable to the second antenna array, the receive circuit is configured to receive the radio frequency response or the microwave frequency response detected by the second antenna array;
a system on chip module configured to integrate the non-invasive analyte sensor system in a single module;

a power source arranged between a second side of the printed circuit board and the first wall of the housing, the power source comprising a battery; and at least one electromagnetic shield arranged between the first side of the printed circuit board and both the first antenna array and the second antenna array, wherein the at least one electromagnetic shield separates the internal space of the housing into a first portion and a second portion, wherein the at least one electromagnetic shield electromagnetically isolates the transmit circuit, the receive circuit, the system on chip module, and the printed circuit board in the first portion from other internal components of the non-invasive analyte sensor system in the second portion.

19. The non-invasive analyte sensor of claim 18, wherein the two or more antennas of the first antenna array comprises an antenna having a rectangular shape and an antenna having a rounded rectangle shape.

20. The non-invasive analyte sensor of claim 18, wherein the two or more antennas of the second antenna array comprises an antenna having a rounded rectangle shape and an antenna having a stadium shape.

21. The non-invasive analyte sensor of claim 18, wherein the two or more antennas of the first antenna array comprises a first antenna and a second antenna separated by a first space, and wherein the two or more antennas of the second antenna array comprises a third antenna and a fourth antenna separated by a second space, wherein the first antenna array and the second antenna array are separated by a third space, wherein the third space is greater than the first space and is greater than the second space.

22. The non-invasive analyte sensor of claim 18, wherein the first antenna array and the second antenna array are arranged on the same plane.

* * * * *